United States Patent
Lacoste et al.

(10) Patent No.: US 9,778,201 B2
(45) Date of Patent: Oct. 3, 2017

(54) CAPSULE OR CORK COMPRISING SECURITY FEATURES

(75) Inventors: Russell R. Lacoste, Mount Pleasant, SC (US); Stephen Wass, Annapolis, MD (US); James Bonhivert, Clifton, VA (US); Toni Lee Gazaway, Stafford, VA (US); Sarah Yacoub, Washington, DC (US); Thomas Classick, Fairfax Station, VA (US)

(73) Assignee: SICPA HOLDING SA, Prilly (CH)

( * ) Notice: Subject to any disclaimer, the term of this patent is extended or adjusted under 35 U.S.C. 154(b) by 48 days.

(21) Appl. No.: 14/412,561

(22) PCT Filed: Jul. 3, 2012

(86) PCT No.: PCT/US2012/045404
§ 371 (c)(1),
(2), (4) Date: Jan. 2, 2015

(87) PCT Pub. No.: WO2014/007807
PCT Pub. Date: Jan. 9, 2014

(65) Prior Publication Data
US 2015/0185160 A1      Jul. 2, 2015

(51) Int. Cl.
*G01N 21/84*   (2006.01)
*B65D 41/00*   (2006.01)
(Continued)

(52) U.S. Cl.
CPC .......... *G01N 21/84* (2013.01); *B41M 3/144* (2013.01); *B42D 25/29* (2014.10); *B42D 25/378* (2014.10); *B65D 39/00* (2013.01); *B65D 41/00* (2013.01); *B65D 41/58* (2013.01); *B65D 51/245* (2013.01); *G01N 21/55* (2013.01); *B41M 1/18* (2013.01); *B41M 1/22* (2013.01); *B41M 1/38* (2013.01); *B41M 3/008* (2013.01); *B41M 5/0041* (2013.01);
(Continued)

(58) Field of Classification Search
None
See application file for complete search history.

(56) References Cited

U.S. PATENT DOCUMENTS

| 896,095 A | 8/1908 | Erwin |
| 2,806,620 A * | 9/1957 | Blanch .................. B65D 41/62 215/251 |

(Continued)

FOREIGN PATENT DOCUMENTS

| CN | 2399323 | 10/2000 |
| DE | 19525503 | 1/1997 |

(Continued)

OTHER PUBLICATIONS

English-Language translation of Georgian Office Action in related Georgian Application No. 13711/01, dated Nov. 2, 2015

*Primary Examiner* — Shawn Decenzo
(74) *Attorney, Agent, or Firm* — Greenblum & Bernstein, P.L.C.

(57) ABSTRACT

A capsule placed on a beverage bottle. The capsule includes a capsule material layer and at least two layers of security ink on the capsule material layer. Each of the at least two layers has a different chemical composition. At least one layer of the at least two layers includes a first composition having flakes exhibiting full reflection of light received at a predetermined wavelength.

24 Claims, 11 Drawing Sheets

(51) Int. Cl.

| | | |
|---|---|---|
| *B41M 3/14* | (2006.01) | |
| *B42D 25/29* | (2014.01) | |
| *B65D 41/58* | (2006.01) | |
| *G01N 21/55* | (2014.01) | |
| *B65D 39/00* | (2006.01) | |
| *B65D 51/24* | (2006.01) | |
| *B42D 25/378* | (2014.01) | |
| *B41M 1/18* | (2006.01) | |
| *B41M 1/22* | (2006.01) | |
| *B41M 1/38* | (2006.01) | |
| *B41M 3/00* | (2006.01) | |
| *B41M 5/00* | (2006.01) | |
| *B42D 25/324* | (2014.01) | |
| *B42D 25/382* | (2014.01) | |
| *B42D 25/387* | (2014.01) | |
| *B42D 25/391* | (2014.01) | |
| *G01N 21/90* | (2006.01) | |

(52) U.S. Cl.
CPC ......... *B41M 5/0076* (2013.01); *B42D 25/324* (2014.10); *B42D 25/382* (2014.10); *B42D 25/387* (2014.10); *B42D 25/391* (2014.10); *B42D 2033/16* (2013.01); *B42D 2033/18* (2013.01); *B42D 2033/20* (2013.01); *B42D 2033/24* (2013.01); *B42D 2033/26* (2013.01); *B65D 2203/00* (2013.01); *G01N 21/909* (2013.01)

(56) References Cited

U.S. PATENT DOCUMENTS

| | | | |
|---|---|---|---|
| 4,344,987 A | 8/1982 | Ostertag et al. | |
| 4,475,661 A | 10/1984 | Griffin | |
| 4,705,300 A | 11/1987 | Berning et al. | |
| 4,705,356 A | 11/1987 | Berning et al. | |
| 4,721,217 A * | 1/1988 | Phillips | B65D 55/066 206/459.1 |
| 4,779,898 A | 10/1988 | Berning et al. | |
| 4,930,866 A | 6/1990 | Berning et al. | |
| 4,978,394 A | 12/1990 | Ostertag et al. | |
| 5,084,351 A | 1/1992 | Philips et al. | |
| 5,172,460 A * | 12/1992 | Womack | B65D 41/62 215/251 |
| 5,401,306 A | 3/1995 | Schmid et al. | |
| 5,624,468 A | 4/1997 | Lake | |
| 5,654,022 A * | 8/1997 | Sayre | B65D 41/62 215/251 |
| 6,254,139 B1 * | 7/2001 | Fresnel | B65D 55/026 283/72 |
| 6,565,770 B1 | 5/2003 | Mayer et al. | |
| 6,589,445 B2 | 7/2003 | Sugiyama et al. | |
| 8,864,037 B2 * | 10/2014 | Callegari | B32B 15/08 235/454 |
| 2007/0224341 A1 | 9/2007 | Kuntz et al. | |
| 2008/0140432 A1* | 6/2008 | Fenn | G06Q 30/018 705/317 |
| 2009/0045959 A1* | 2/2009 | Adstedt | B65D 55/028 340/572.3 |
| 2010/0112314 A1* | 5/2010 | Jiang | C09D 11/50 428/199 |
| 2010/0178508 A1 | 7/2010 | Kasch et al. | |
| 2010/0200649 A1 | 8/2010 | Callegari et al. | |
| 2010/0307376 A1 | 12/2010 | Aboutanos et al. | |
| 2011/0293899 A1 | 12/2011 | Tiller et al. | |

FOREIGN PATENT DOCUMENTS

| | | |
|---|---|---|
| EP | 708154 | 4/1996 |
| EP | 0847432 | 6/1998 |
| EP | 0967156 | 12/1999 |
| EP | 1857374 | 11/2007 |
| GB | 798284 | 7/1958 |
| RU | 19525 U1 | 9/2001 |
| RU | 42033 U1 | 11/2004 |
| RU | 106226 U1 | 7/2011 |
| RU | 2463656 C1 | 10/2012 |
| WO | WO93/22397 | 11/1993 |
| WO | WO94/22976 | 10/1994 |
| WO | WO95/22586 | 8/1995 |
| WO | WO2006/134030 | 12/2006 |
| WO | WO2008/033059 | 3/2008 |
| WO | WO2008092522 | 8/2008 |
| WO | WO2010040415 | 4/2010 |

\* cited by examiner

CAPSULE OR CORK COMPRISING SECURITY FEATURES

FIELD OF THE INVENTION

Embodiments of the invention relate to the field of protection of wine bottles against fraudulent diversion or counterfeiting. Embodiments of the invention also relate to a new marking which does not significantly affect or even form a part of the global design of a wine bottle, providing an efficient and discrete high level of protection.

BACKGROUND OF THE INVENTION

Wine is a favorite beverage consumed daily around the world, as well as included as part of specific occasions, such as weddings and/or birthdays, for example. It is also a business, which generates billions of dollars per year. There is a wide spectrum of wines of different values, whose value and cost may widely vary.

Counterfeit consumer goods are imitation products offered for sale that are intended to either deceive the consumer or to take unfair advantage of the renown of the brand name. The spread of counterfeit goods has become global in recent years and the variety of such counterfeiting has increased significantly.

In the case of wine fraud, inferior wines are passed off or sold to a customer, usually at a price higher than what the product is worth. Such illicit products may cause sickness due to harmful chemicals being included in the wine. In recent years, much attention has been focused on label fraud, where counterfeit labels from cult wines and other rare and expensive wines, for example, are affixed to bottles of less expensive wine, and then resold. Wine fraud can also involve less expensive wines, for example, if they are sold in large volumes. Wine Spectator noted that some experts suspect that as much as 5% of the wine sold in secondary markets could be counterfeit.

As noted above one form of fraud involves affixing counterfeit labels of expensive wines to bottles of less expensive wine. Initially, label fraud mostly consisted of taking a wine from a region of lesser acclaim (such as Southwest France or Calabria in Italy) and then labeling the wine as if it came from more prestigious regions such as Bordeaux or Tuscany. To counter this type of fraud, governments developed extensive appellation systems and Protected Designations of Origin or (PDOs) that attempted to regulate wines labeled as coming from particular wine regions. Early attempts to protect the name of a wine region lead to government declarations on the boundaries and wines permitted to carry the names of Chianti, Oporto and Tokaji. Today most major European wine producing countries utilize some appellation system of protected origins. The most well-known systems include the Appellation d'Origine Contrôlée (AOC) used in France, the Denominazione di Origine Controllata (DOC) used in Italy, the Denominação de Origem Controlada (DOC) used in Portugal, and the Denominación de Origen (DO) system used in Spain. Producers who are registered in association with each appellation must abide by the appellation's rules, including exact percentage of grapes (often 100%) that must come from that region. Producers who fraudulently use grapes from outside the region they are proclaiming on their wine labels can be pursued by the appellation's authorities.

As it became more difficult to fraudulently label wines with the wrong provenance, label fraud soon evolved to the pilfering of the identities of wine estates themselves. Merchants would take the bottles of lesser priced wines and label them with the names of the finest classified Bordeaux estates or Grand crus of Burgundy. Thus, the temptation remains very high to replace one famous or expensive wine with another cheaper wine, for example. This unfair behavior misleads the consumer, who believes they are buying a good wine quality, but actually acquires a fake wine.

Although consumers are the prime victims of the blight of counterfeit and illicit trade, rights holders also suffer significant impacts. This can be both economically, from the loss of sales and revenue, due to forgery and use forgeries, and also in that penal liability for unfit products can be imputed to the apparent rights holders. They then have to establish their innocence to avoid claims for damages and invest significant effort to re-establish brand image as well as to ensure countermeasures are taken against the true culprits of the illicit trade.

Attempts to solve this issue have been the subject of intensive study since 1900. U.S. Pat. No. 896,095A discloses a thin strip of glass of less width than the bottle, attached at one end only to a side of the bottle near the bottom and extending above the mouth thereof; the extending portion, after the bottle is filled and corked, is caused to bend down over the stopper by softening the strip at a suitable point by heat. The name of the proprietor or manufacturer, or the name of the preparation may be impressed on the strip instead of the bottle, and as the strip is destroyed when bottle is opened, the bottle cannot be used, again without detection.

Today sophisticated methods exist to avoid diversion and/or counterfeiting which are extensively used. For example, an RFID tag may be attached to the bottle, or the capsule on the bottle, which provides conventional protection for a wine bottle. Additionally, a barcode or an alpha-numeric identifier may be used, as well as holograms and tamper evident structures. These technologies, however, all have a common drawback, in that these technologies are at least partially visible, thus possibly affecting the global appearance and design of the bottle and its label paper, which also serves as an identifier of the origin of the wine bottle.

There remains, however, a need to provide not only a solution that is not visible to the unaided eye, but also a solution that will not affect or even necessarily form a part of the original design of the bottle (or is at least be less invasive), while also ensuring such security features have a high level of security and/or coding properties to guard against forgery and are able to provide track-and-trace information for the bottles produced around the world.

SUMMARY OF EMBODIMENTS OF THE INVENTION

Embodiments of the present invention provide a solution that may be visible or invisible to the unaided eye, and does not significantly affect the original design of the bottle (or is at least less invasive than existing solutions). Additionally, embodiments of the present invention ensure such security features have a high level of security and/or coding properties against forgery and are able to provide authentication and/or track-and-trace information for bottles produced around the world.

By implementing embodiments of the present invention, a wine closure (e.g., a wine capsule material layer) is printed with one or more layers of inks (e.g., security inks) as a security feature, to provide an identifier, (e.g., a unique identifier) for authenticating a wine bottle. In accordance with aspects of embodiments of the present invention, the security features have a high level of security and coding properties against forgery. In embodiments, the relative positions of the one or more layers of inks and the capsule material layer provide a synergistic effect with regard to the light reflected from and/or emitted from the capsule/ink layer arrangement.

Aspects of the present invention are directed to a capsule (or cork) placed on a beverage bottle. The capsule (or cork) comprises a capsule (or cork) material layer and at least two layers of security ink on the capsule material layer. Each of the at least two layers has a different chemical composition. At least one layer of the at least two layers comprises a first composition having flakes exhibiting full reflection of light received at a predetermined wavelength.

In embodiments of the invention, at least one second layer of the at least two layers comprises a second composition having flakes exhibiting semi-reflection of light received at the predetermined wavelength.

In embodiments of the invention, the capsule further comprises a luminescent layer comprising a third composition containing at least one luminescent pigment.

In further embodiments of the invention, the flakes exhibiting full reflection constitute between about 3 to 25% based on a total weight of the first composition.

In additional embodiments of the invention, the flakes exhibiting the semi-reflection constitute between about 3 to 25% based on a total weight of the second composition.

In yet further embodiments of the invention, the at least one luminescent pigment is comprised in said luminescent layer between 3 to 25% based on a total weight of the third composition.

In embodiments of the invention, each layer of the at least two layers has a different selective reflection band of the light while illuminated at the predetermined wavelength.

In further embodiments of the invention, the at least one layer comprising the flakes exhibiting the full reflection is arranged adjacent and located below the at least one second layer comprising the flakes exhibiting the semi-reflection.

In additional embodiments of the invention, the luminescent layer is arranged in contact with the capsule (or cork) material layer.

In yet further embodiments of the invention, the capsule (or cork) material layer is covered by an embossed multilayer security ink system.

In embodiments of the invention, the capsule material layer is structured and arranged on the bottle such that at least a portion of the capsule material layer is damaged upon removal of the capsule material layer from the bottle.

In further embodiments of the invention, upon receiving the light, the at least one layer comprising the flakes having the full reflection is structured and arranged to provide a reflecting light to the at least one second layer to backlight the at least one second layer.

In additional embodiments of the invention, the reflecting light provides an authenticatable signature to authenticate at least one of the capsule (or cork) and the beverage bottle.

In further embodiments of the invention, the cork arrangement further comprises a receiving layer.

In embodiments of the invention, the luminescent layer is arranged in contact with the cork material layer.

In further embodiments of the invention, the receiving layer is arranged in contact with the cork material layer.

In additional embodiments of the invention, the receiving layer is further arranged in contact with the bottle, such that such that at least a portion of the receiving layer is damaged upon removal of the cork from the bottle.

In embodiments of the invention, the at least two layers of security ink on the cork material layer are arranged in an area of the cork material exposed by the bottle.

In further embodiments of the invention, the at least two layers of security ink on the cork material layer are arranged on a surface of the cork material layer and on a surface of the bottle.

In additional embodiments of the invention, upon receiving the light, the at least one layer comprising the flakes exhibiting the full reflection is structured and arranged to provide a reflecting light to the at least one second layer to back light the at least one second layer.

Embodiments of the present invention are additionally directed to a method of authenticating a capsule (or cork) placed on a beverage bottle, the capsule (or cork) comprising a capsule (or cork) material layer, and at least two layers of security ink on the capsule (or cork) material layer. Each of the at least two layers has a different chemical composition. At least one layer of the at least two layers comprises a first composition having flakes exhibiting full reflection of light received at a predetermined wavelength. The method comprises illuminating the capsule (or cork) with the light at the predetermined wavelength, detecting a reflected light, which is reflected by the at least one layer comprising the flakes exhibiting the full reflection and transmitted through the at least one second layer as a back light to the at least one second layer; and comparing the reflected light to a predetermined value to authenticate the capsule (or cork).

Further embodiments of the present invention are directed to a multilayer structure, comprising a carrier material layer and at least two layers of security ink on the carrier material layer. Each of the at least two layers has a different composition. At least one layer of the at least two layers comprises a first composition containing flakes exhibiting full reflection of light received at a predetermined wavelength.

In embodiments of the invention, the luminescent layer is arranged in contact with the carrier material layer.

In embodiments of the invention, a capsule or cork to be used as a closure of a container comprises the multilayer structure.

In further embodiments of the invention, a capsule or cork to be used as a closure of a beverage bottle comprises the multilayer structure.

In additional embodiments of the invention, a capsule comprises the multilayer structure.

In yet further embodiments of the invention, the carrier material layer is a capsule material layer.

In further embodiments of the invention, a container carries a capsule (or cork) as a closure.

In yet further embodiments of the invention, the at least two layers of security ink on the cork material layer are arranged in an area of the cork material exposed by the container.

In embodiments of the invention, the at least two layers of security ink on the cork material layer are arranged in an area of the cork material layer and in an area of the bottle.

In additional embodiments of the invention, the container is a beverage bottle.

Additional embodiments of the invention are directed to a method of marking a capsule or a cork contained in a beverage container, the method comprising depositing a multilayered ink system onto the capsule or cork, wherein the depositing comprises sequentially marking the capsule or cork with a plurality of layers to form the multilayered ink system.

In additional embodiments of the invention, the capsule material layer is structured and arranged as a screw top.

In additional embodiments of the invention, the one or more of the at least two layers of security ink provide a track-and-trace signature for at least one of the capsule and the beverage bottle.

These and other features and advantages of the present invention will be more readily understood from a reading of the following detailed description by those of ordinary skill in the art. It is to be appreciated that certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, references to values stated in ranges include each and every value within that range.

BRIEF DESCRIPTION OF THE DRAWINGS

For a more complete understanding of the invention, as well as other objects and further features thereof, reference may be had to the following detailed description of the invention in conjunction with the following exemplary and non-limiting drawings wherein.

Figure 1:
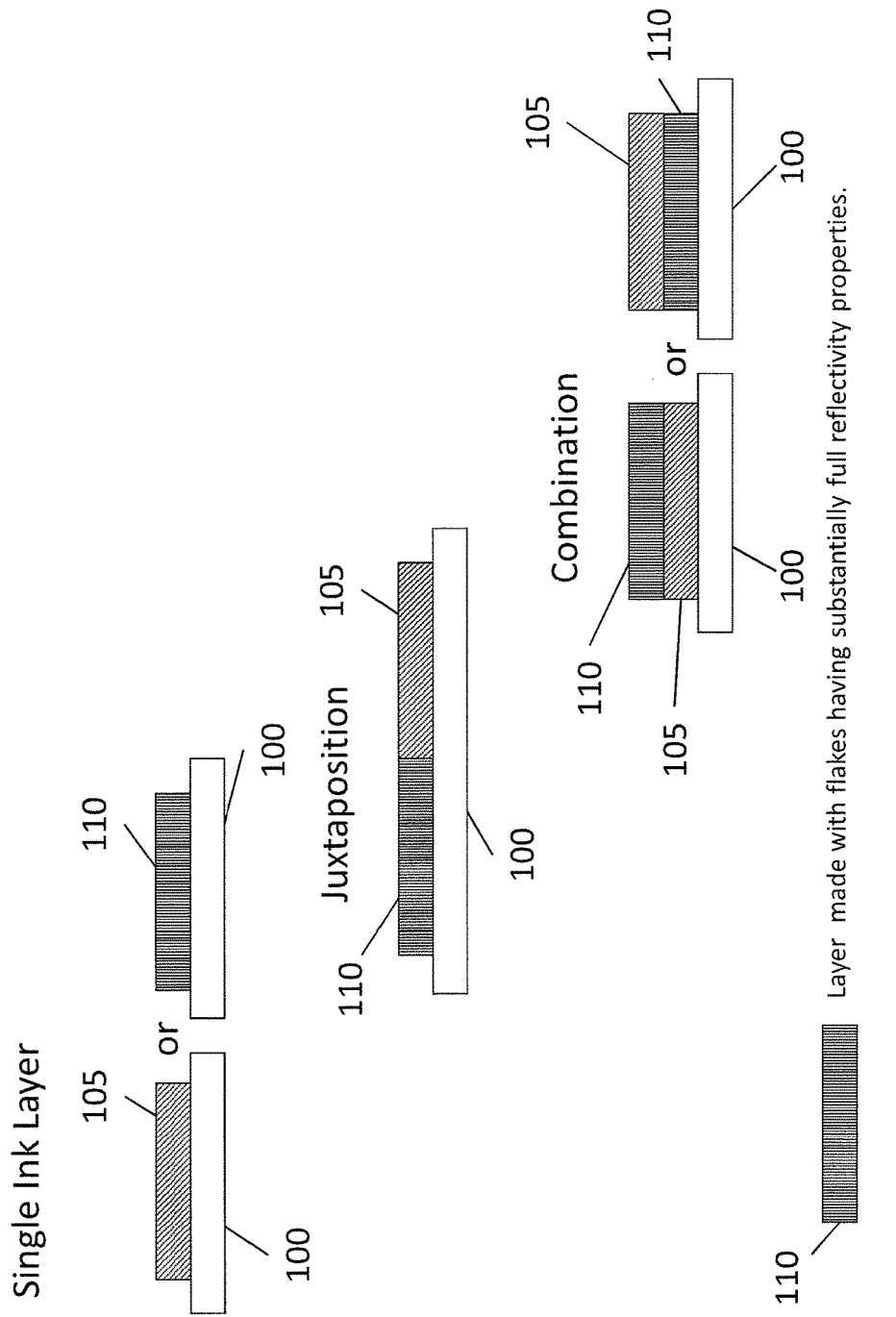
FIG. 1 illustrates exemplary schematic depictions of different layer arrangements in accordance with embodiments of the invention.

Reference numbers refer to the same or equivalent parts of the present invention throughout the various figures of the drawings.

DETAILED DESCRIPTION OF EMBODIMENTS OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention, including embodiments of flakes and films, may be embodied in practice.

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise. For example, reference to "a magnetic material" would also mean that mixtures of one or more magnetic materials can be present unless specifically excluded.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

The various embodiments disclosed herein can be used separately and in various combinations unless specifically stated to the contrary.

Wine Bottle

A wine bottle is a bottle used for holding wine, generally made of glass. Some wines are fermented in the bottle, while others are bottled only after fermentation. Recently, the bottle has become a standard unit of volume to describe sales in the wine industry, measuring 750 ml. However, bottles are produced in a variety of volumes and shapes.

Traditional colors used for wine bottles include, for example, dark green, medium green, light green, amber and clear. Clear colorless bottles have recently become popular with white wine producers in many countries. Dark-colored bottles are most commonly used for red wines, but many white wines also still come in dark green bottles. One reason for using colored or tinted glass is that natural sunlight can break down desirable antioxidants such as vitamin C and tannins in a wine over time, which impacts storability and can cause a wine to prematurely oxidize. Dark glass can prevent oxidation and increase storage life. Thus, for example, it is mostly ready-to-drink white wines with a short anticipated storage lifespan that are bottled in clear colorless bottles.

Most wines are sealed using corks. Wine corks can be made of either a single piece of cork, or composed of particles, as in champagne corks; corks made of granular particles are called "technical corks." Natural cork closures are used for about 60%-80% of the 20 billion bottles of wine produced each year.

Because of the cellular structure of cork, it is easily compressed upon insertion into a bottle and will expand to form a tight seal. The interior diameter of the neck of glass bottles tends to be inconsistent, making this ability to seal through variable contraction and expansion an important attribute. However, unavoidable natural flaws, channels, and cracks in the bark make the cork itself highly inconsistent.

An increasing number of wine producers have been using alternative closures such as screw caps, or synthetic plastic "corks." Alternative wine closures are substitute closures used in the wine industry for sealing wine bottles in place of traditional cork closures. The emergence of these alternatives has grown in response to quality control efforts by winemakers to protect against "cork taint" caused by the presence of the chemical trichloroanisole (TCA). In addition to being less expensive, alternative closures prevent cork taint, although they have been blamed for other problems such as excessive reduction.

A screw cap or "Stelvin cap" is a closure made, for example, from aluminum material that threads onto the bottleneck. Screw caps a tighter seal and can keep out oxygen for a longer time than cork. These benefits aid in maintaining the wine's overall quality and aging potential. In some countries, screw caps are often seen as a cheap alternative destined only for the low-grade wines; however, these alternatives to real cork have their own properties, some advantageous and others controversial. For example, while screw caps are generally considered to offer a trichloroanisole (TCA) free seal, they reduce the oxygen transfer rate to almost zero, which can lead to reductive qualities in the wine. Thus, a disadvantage of screw caps is reduction, i.e., the opposite of oxidation, which may suppress a wine's aroma and possibly cause unpleasant ones. Thus, natural cork stoppers are important because they allow oxygen to interact with wine for proper aging, and are best suited for bold red wines purchased with the intent to age. Moreover, while TCA is one of the primary causes of cork taint in wine, in recent years major cork producers have developed methods that remove most TCA from natural wine corks.

Synthetic corks are made from plastic compounds designed to look and "pop" like natural cork, but without the risk of TCA contamination. Disadvantages of some wine synthetic corks include a risk of harmful air entering a bottle after only 18 months, as well as the difficulty in extracting them from the bottle and using the plastic cork to reseal the wine. Some can also impart a slight chemical flavor to the wine. Unlike natural corks, many wine synthetic corks are made from material that is not biodegradable, but is recyclable in many communities.

As noted above, most wine bottles are sealed with a cork, although screw caps are increasingly being utilized. Corked wine bottles typically have a protective sleeve called a capsule (also referred to as a "foil") covering the top of the bottle, e.g., the cork and part of the neck of a wine bottle. One purpose of the capsule is to protect the cork from being gnawed away, for example, by rodents, or infested with the cork weevil. Additionally, the capsule may serve as collar to catch small drips of wine when pouring. The capsule also serves as a decorative element of the bottle's label.

Capsules were historically made of lead. Due to research showing that trace amounts of toxic lead could remain on the lip of the bottle and mix with the poured wine, however, lead capsules (e.g., lead foil bottleneck wrappings) were slowly phased out and by the 1990s most capsules were made of tin, heat-shrink plastic (polyethylene or PVC), or aluminum or polylaminate aluminum, for example. Sealing wax may also be used sometimes in addition to, or in lieu of, the capsule, or the capsule can be omitted entirely.

Overview of Security Ink Layers

In accordance with aspects of the invention, the capsule may also serve to indicate tampering, or label fraud. That is, a capsule is difficult to remove from the wine bottle without damaging the integrity thereof. For example, when opening the wine bottle, the integrity of the capsule is (at least partially) destroyed by removing the cork. Moreover, due to the neck shape of a conventional wine bottle (i.e., the thickened portion at the opening) a capsule cannot simply be slipped or pulled off. Thus, in embodiments, the capsule serves as an indicator of tampering, or label fraud. More specifically, in embodiments, one or more layers of inks are, e.g., printed on the capsule material layer. In embodiments, the one or more layers may include a layer having a first composition having flakes exhibiting partial reflection of light received at a predetermined wavelength and/or a layer having flakes exhibiting full reflection of light received at a predetermined wavelength. Additionally, in embodiments, the one or more layers may include a luminescent layer (e.g., a WB Gravure printed invisible fluorescent ink). In further embodiments, the one or more layers may include an absorption layer, for example, a dark (e.g., black) layer of ink (e.g., an infrared absorbing (IRA) black ink, an infrared transparent (IRT) black ink or a combination thereof). In further embodiments, the one or more layers may include a metallic gold layer of ink, which may also include one or more machine readable (MR) features.

In accordance with aspects of embodiments of the invention, the combination of the capsule material with the one or more ink layers, can produce synergistic effects with regard to the appearance (e.g., distinctiveness) of the multilayer capsule/ink structure.

With an exemplary embodiment, a capsule placed on a beverage bottle comprises a capsule material layer and at least two layers of security ink on the capsule material layer. Each of the at least two layers has a different chemical composition. At least one layer of the at least two layers comprises a first composition having flakes exhibiting semi-reflection (or partial reflection) of light received at a predetermined wavelength. In further embodiments, at least one second layer of the at least two layers comprises a second composition having flakes exhibiting full-reflection of light received at the predetermined wavelength.

FIG. 1 illustrates exemplary schematic depictions of different layer arrangements. In accordance with aspects of the invention, a layer of ink may be arranged as a single layer, in a juxtaposed configuration and/or in a partially or fully overlapping configuration with respect to the other layers. For example, as shown in FIG. 1, with a single layer arrangement, a layer of ink (e.g., a layer of ink 105 comprising flakes having semi-reflective properties or a layer of ink 110 comprising flakes having substantially full reflective properties), may be arranged as a single layer on a substrate 100 (e.g., a capsule material layer, cork, a polymer layer, a paper layer, or a fabric layer, amongst other contemplated substrates). With a single layer configuration, the single layer presents its own properties alone and may present a synergistic effect with the substrate 100 (e.g., a wine capsule material layer).

As shown in FIG. 1, with a juxtaposed arrangement, two or more layers of ink (e.g., a layer of ink 105 comprising flakes having semi-reflective properties and a layer of ink 110 comprising flakes having substantially full reflective properties), may be configured in a juxtaposed (or side-by-side) arrangement on a substrate 100 (e.g., a capsule material layer, cork, a polymer layer, a label layer or a fabric layer, amongst other contemplated substrates). With a juxtaposed arrangement, each of the one or more layers presents its own properties alone and may present a synergistic effect with the substrate (e.g., the wine capsule material layer), without necessarily presenting a synergetic or bonus effect with the other adjacent ink layers. Some synergetic effect with the other adjacent ink layers may be provided in transition regions between adjacent ink layers. Moreover, each layer which has specific color shift properties may have specific λ max of reflectance, which could constitute a unique identifier in itself in addition to the layers' color shifting properties.

As shown in FIG. 1, with a combination arrangement, two or more layers of ink (e.g., a layer of ink 105 comprising flakes having semi-reflective properties and a layer of ink 110 comprising flakes having substantially full reflective properties), may be configured in an overlapping arrangement on a substrate 100 (e.g., a capsule material layer, cork, a polymer layer, a label layer, or a fabric layer, amongst other contemplated substrates). In accordance with aspects of embodiments of the invention, with a combined layer arrangement (e.g., partially or fully overlapping ink layers), in embodiments, each ink layer presents its own properties, while the combination of two or more of the overlapping ink layers provides a synergetic effect.

Figure 2:
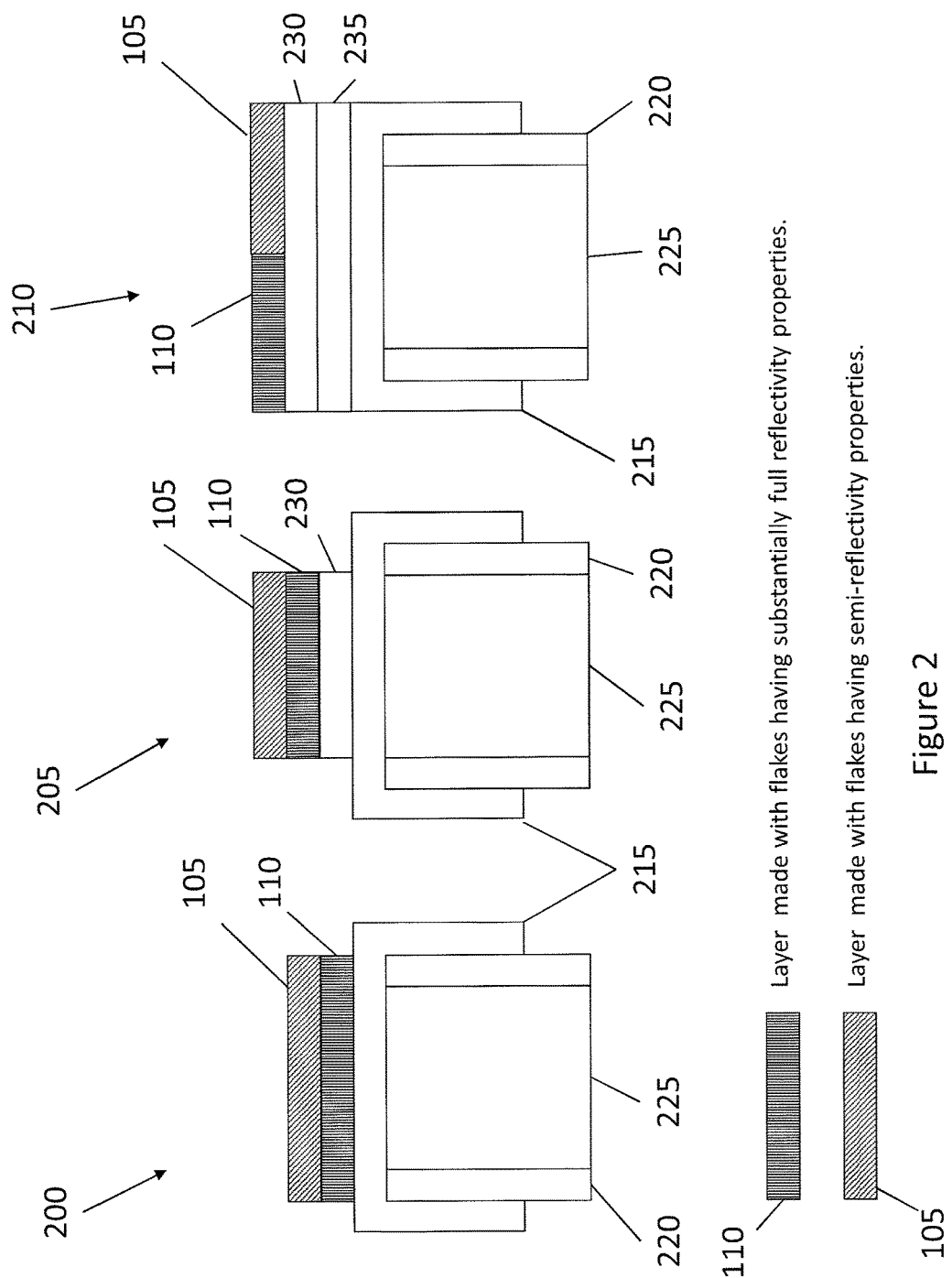
FIG. 2 illustrates exemplary schematic depictions of different layer arrangements on a capsule layer in accordance with embodiments of the invention.

FIG. 2 illustrates exemplary schematic depictions of different layer arrangements 200, 205, 210 on a capsule layer in accordance with embodiments of the invention. As shown with exemplary arrangement 200, a bottle 220 (e.g., a wine bottle) includes a cork 225 (e.g., a cork or a synthetic plastic "cork") and a capsule material layer 215 arranged over the bottle 220 and cork 225. (As should be understood, for clarity and understanding of the drawings, the schematic illustration of FIG. 2 does not illustrate the bottle 220 as having the above-mentioned thickened neck portion at the bottle orifice.) As shown with arrangement 200, a layer of ink 110 comprising flakes having substantially full reflective properties is arranged (e.g., printed) on the capsule material layer 215. Additionally, with arrangement 200, a layer of ink 105 comprising flakes having semi-reflective properties is arranged (e.g., printed) on the layer of ink 110.

As shown with exemplary arrangement 205, a luminescent layer 230 is arranged (e.g., printed) on the capsule material layer 215, the layer of ink 110 comprising flakes having substantially full reflective properties is arranged (e.g., printed) on the luminescent layer 230, and the layer of ink 105 comprising flakes having semi-reflective properties arranged (e.g., printed) on the layer of ink 110.

As shown with arrangement 210, an absorptive layer 235 (e.g., a black ink layer) is arranged (e.g., printed) on the capsule material layer 215, and the luminescent layer 230 is arranged (e.g., printed) on the absorptive layer 235. Additionally, as shown with exemplary arrangement 210, the layer of ink 110 comprising flakes having substantially full reflective properties and the layer of ink 105 comprising flakes having semi-reflective properties are arranged (e.g., printed) on the luminescent layer 230 in a juxtaposed manner.

As further illustrated in FIG. 2, in accordance with aspects of embodiments of the invention, the extent to which the one or more layers cover the approximately circular top area of the capsule material layer 215 may be varied. For example, with arrangement 205, the ink layers 105, 110, 230 cover a central portion of the top area of the capsule material layer 215 (e.g. to approximately correspond with the diameter of the cork). In contrast, with arrangement 210, the ink layers 230, 235, and 105 and 110 together, cover an entire top area of the capsule material layer 215. With arrangement 200, the ink layers 105, 110 cover a larger central portion of the top area of the capsule material layer 215 than as compared to arrangement 205 (e.g. to approximately correspond with the outer diameter of the bottle neck).

Figure 3:
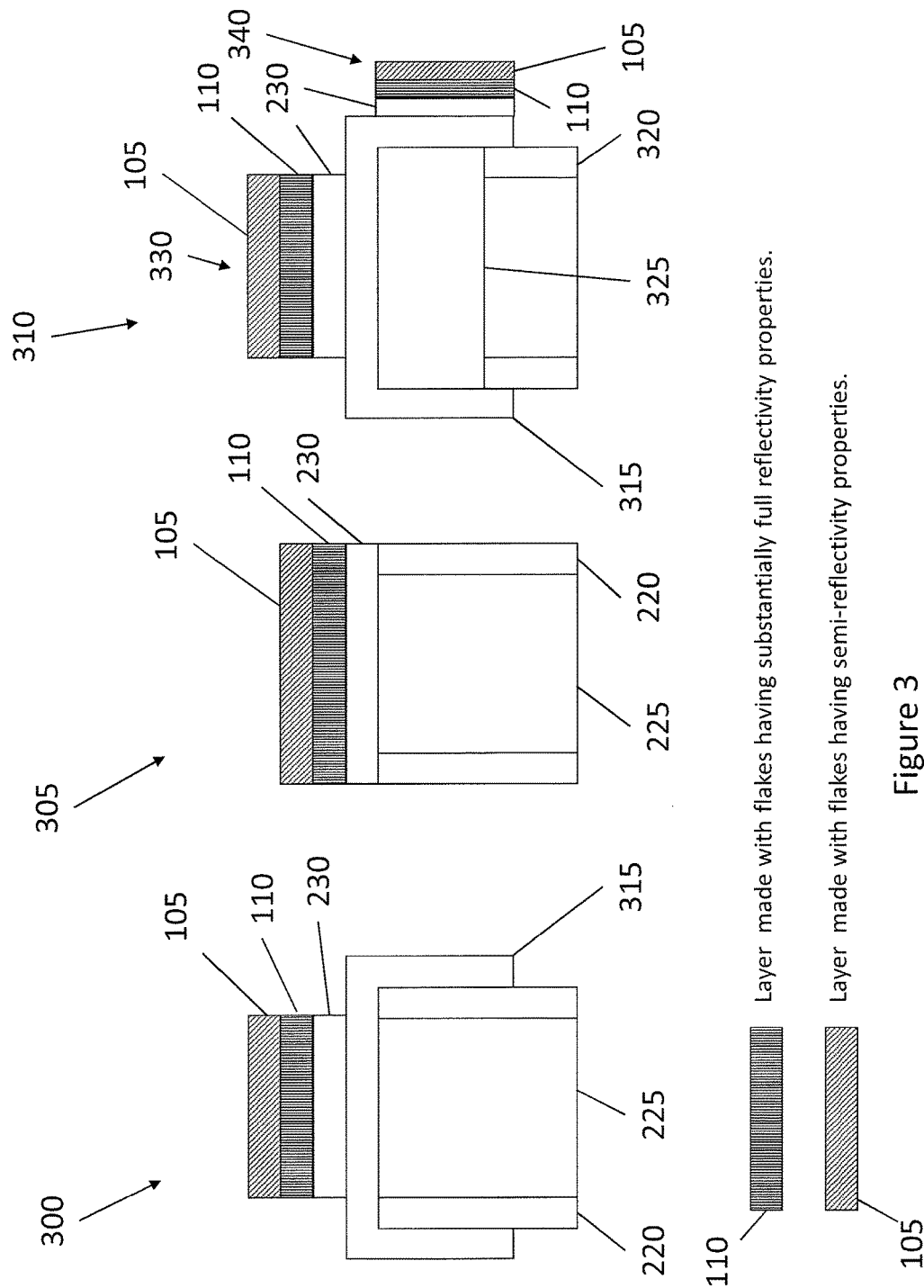
FIG. 3 illustrates exemplary schematic depictions of different layer arrangements on bottles without capsules in accordance with embodiments of the invention.

FIG. 3 illustrates exemplary schematic depictions of different layer arrangements on bottles without capsules in accordance with embodiments of the invention. As shown in FIG. 3, exemplary arrangement 300 includes a bottle 220 (e.g., a wine bottle) and a cork 225 (e.g., a cork or synthetic plastic "cork"). However, as is the case with some wine producers, this exemplary arrangement 300 does not include a capsule material layer. With arrangement 300, however, an ink-receiving layer 315 (e.g., a fiber, label, or polymer strip) is arranged over the bottle 220 and cork 225. As shown with exemplary arrangement 300, a luminescent layer 230 is arranged (e.g., printed) on the ink-receiving layer 315, the layer of ink 110 comprising flakes having substantially full reflective properties is arranged (e.g., printed) on the luminescent layer 230, and the layer of ink 105 comprising flakes having semi-reflective properties arranged (e.g., printed) on the layer of ink 110.

As further illustrated in FIG. 3, in accordance with additional aspects of embodiments of the invention, as is the case with some wine producers, exemplary arrangement 305 does not include a capsule material layer and does not include an ink-receiving layer. Thus, with exemplary arrangement 305, the luminescent layer 230 is arranged (e.g., printed) on portions of the cork 225 and the bottle 220 (e.g., glass), the layer of ink 110 comprising flakes having substantially full reflective properties is arranged (e.g., printed) on the luminescent layer 230, and the layer of ink 105 comprising flakes having semi-reflective properties arranged (e.g., printed) on the layer of ink 110.

In accordance with additional aspects of embodiments of the invention, printing of the inks on both the bottle 220 and the cork 225 may allow for an additional level of verification and/or authentication. For example, if the cork position (e.g., relative position in the bottle) has been altered, e.g., due to tampering, the printing on the bottle 220 may no longer align with the printing on the cork 225. Moreover, the layers of ink printed on the bottle 220 may have additional (e.g., in addition to the effects of the inks on the cork 225) synergistic effects in combination with the bottle substrate (e.g., glass).

As further illustrated in FIG. 3, in accordance with additional aspects of embodiments of the invention, as is the case with some wine producers, exemplary arrangement 310 does not include a cork, but rather utilizes a screw cap 325. As shown in FIG. 3, exemplary arrangement 310 includes two security layers (i.e., layers of two or more inks). That is, exemplary arrangement 310 includes an upper security layer 330 and a side security layer 340, which is arranged to cover a separation area between the bottle 320 and the screw cap 325. In a similar manner to exemplary arrangement 300, exemplary arrangement 310 includes an ink-receiving layer 315 (e.g., a fiber, label, or polymer strip) arranged over the bottle 220 and screw cap 325. As shown in exemplary arrangement 310, upper security layer 330 and side security layer 340 each include a luminescent layer 230 arranged (e.g., printed) on the ink-receiving layer 315, the layer of ink 110 comprising flakes having substantially full reflective properties is arranged (e.g., printed) on the luminescent layer 230, and the layer of ink 105 comprising flakes having semi-reflective properties arranged (e.g., printed) on the layer of ink 110. While exemplary arrangement 310 is illustrated with an upper security layer 330 and a side security layer 340, embodiments of the invention contemplate an arrangement only having a side security layer. While exemplary arrangement 310 is illustrated with an ink-receiving layer 315, it should be understood that screw-cap bottles may include a capsule material layer.

Figure 4:
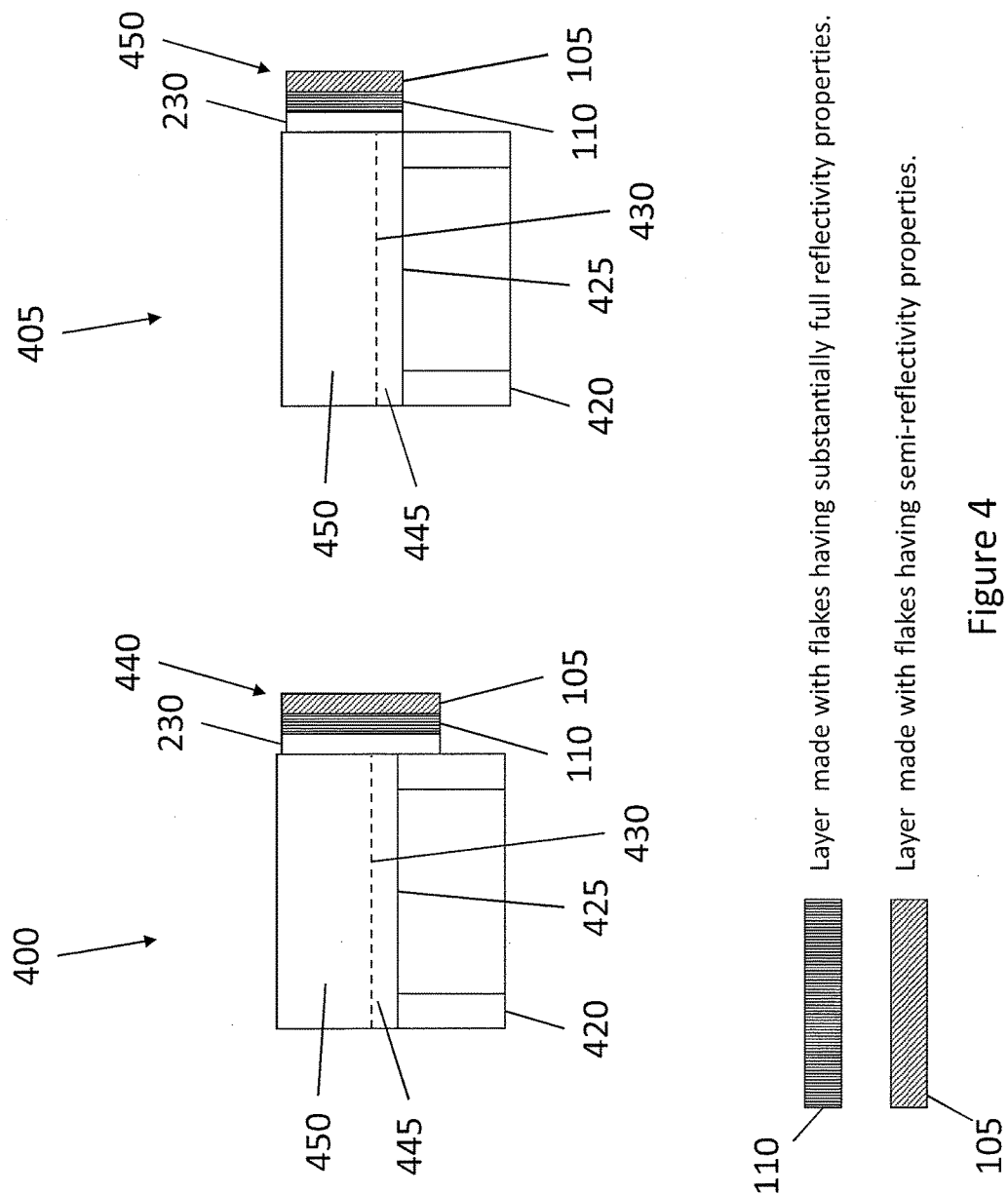
FIG. 4 illustrates exemplary schematic depictions of different layer arrangements on bottles without capsules in accordance with embodiments of the invention.

FIG. 4 illustrates exemplary schematic depictions of different layer arrangements on bottles without capsules in accordance with embodiments of the invention. As shown in FIG. 4, exemplary arrangement 400 includes a bottle 420 (e.g., a wine bottle) and a screw cap 425 with a perforation 430. As should be understood, upon opening the bottle 420 via rotation of the screw cap 425, the screw cap 425 splits at the perforation 430 such that an upper portion 450 of the screw cap 425 can be removed, while the lower portion 445 of the screw cap 425 remains attached to the bottle 420. Exemplary arrangement 400 includes a side security layer 440 arranged to cover a portion of the perforation 430 so as to be damaged upon opening the bottle 420. Additionally, as shown in FIG. 4, the side security layer 440 is arranged to cover a portion of the bottle 420. Side security layer 440 includes a luminescent layer 230 arranged (e.g., printed) on the screw cap 425, the layer of ink 110 comprising flakes having substantially full reflective properties arranged (e.g., printed) on the luminescent layer 230, and the layer of ink 105 comprising flakes having semi-reflective properties arranged (e.g., printed) on the layer of ink 110.

In accordance with additional aspects of embodiments of the invention, printing of the inks on both the screw cap 425 and the bottle 420 may allow for an additional level of verification and/or authentication. For example, if the screw cap position (e.g., relative position on the bottle) has been altered, e.g., due to tampering, the printing on the bottle 420 may no longer align with the printing on the screw cap 425. Moreover, the layers of ink printed on the bottle 420 may have additional (e.g., in addition to the effects of the inks on the screw cap 425) synergistic effects in combination with the bottle substrate (e.g., glass).

As shown in FIG. 4, with exemplary arrangement 405, a side security layer 450 is arranged to cover a portion of the perforation 430 so as to be damaged upon opening the bottle 420. In contrast to side security layer 440 of exemplary arrangement 400, with exemplary arrangement 405, the side security layer 450 is arranged only on the screw cap 425 so as to not cover a portion of the bottle 420. Side security layer 450 includes a luminescent layer 230 arranged (e.g., printed) on the screw cap 425, the layer of ink 110 comprising flakes having substantially full reflective properties arranged (e.g., printed) on the luminescent layer 230, and the layer of ink 105 comprising flakes having semi-reflective properties arranged (e.g., printed) on the layer of ink 110.

Figure 5:
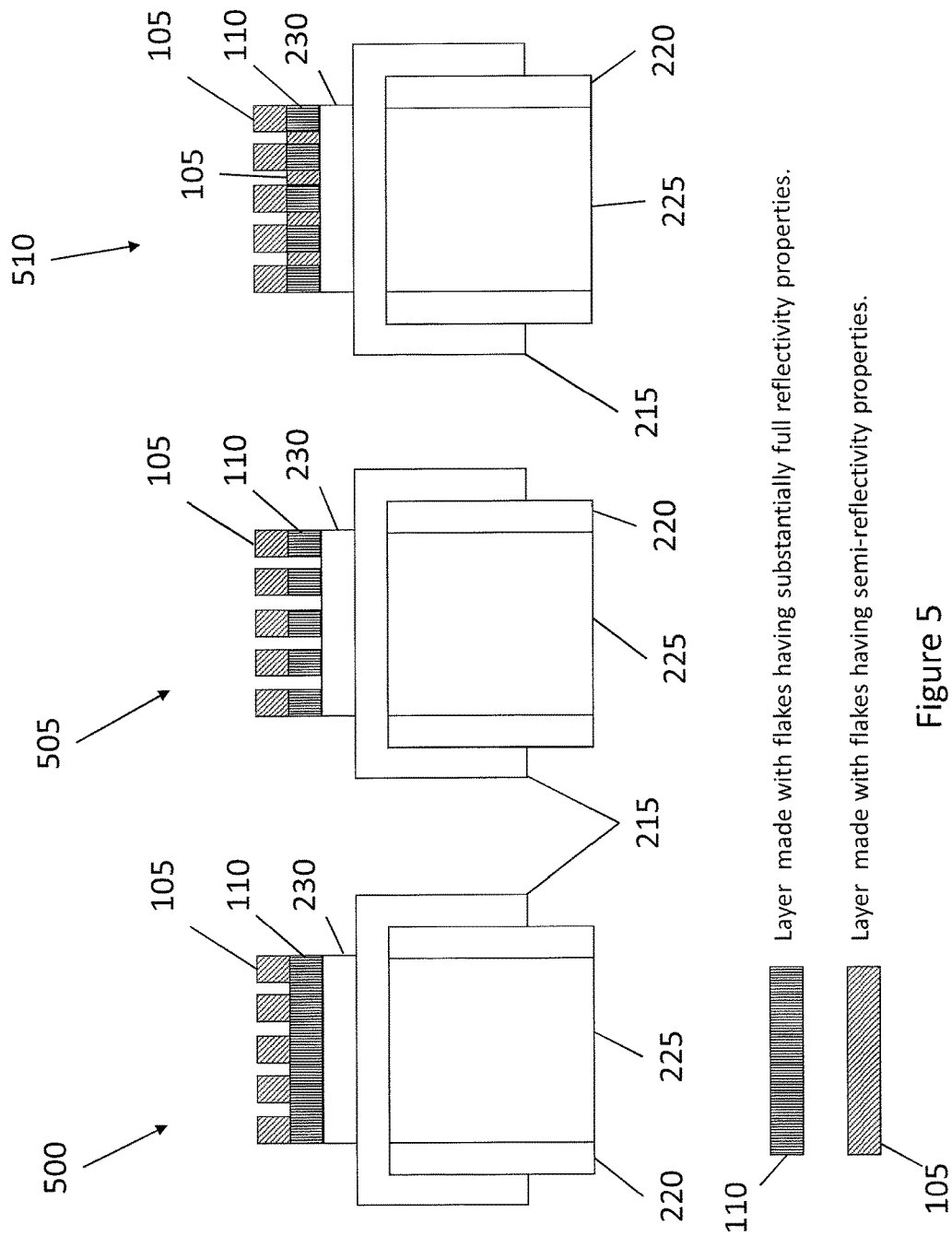
FIG. 5 illustrates exemplary schematic depictions of different layer arrangements on a capsule layer in accordance with embodiments of the invention.

FIG. 5 illustrates exemplary schematic depictions of different layer arrangements 500, 505, 510 on a capsule layer in accordance with embodiments of the invention. As shown in FIG. 5, with exemplary arrangement 500, a bottle 220 (e.g., a wine bottle) includes a cork 225 (e.g., a cork or synthetic plastic "cork") and a capsule material layer 215 arranged over the bottle 220 and cork 225. As shown with exemplary arrangement 500, a luminescent layer 230 is arranged (e.g., printed) on the capsule material layer 215, a layer of ink 110 comprising flakes having substantially full reflective properties is arranged (e.g., printed) on the luminescent layer 230, and a layer of ink 105 comprising flakes having semi-reflective properties is arranged (e.g., printed) on the layer of ink 110. As shown with exemplary arrangement 500, the layer of ink 105 is printed over one or more discrete portions of the layer of ink 110.

With exemplary arrangement 505, the layer of ink 110 comprising flakes having substantially full reflective properties is arranged (e.g., printed) over one or more discrete portions of the luminescent layer 230. The layer of ink 105 comprising flakes having semi-reflective properties is arranged (e.g., printed) in an aligned manner to be arranged only on the layer of ink 110.

With exemplary arrangement 510, the layer of ink 110 comprising flakes having substantially full reflective properties is arranged (e.g., printed) over one or more discrete portions of the luminescent layer 230. The layer of ink 105 comprising flakes having semi-reflective properties is arranged (e.g., printed) over the entire layer of ink 110 such that layer of ink 105 is arranged on the layer of ink 110 and on portions of the luminescent layer 230.

In accordance with additional aspects of embodiments of the invention, each layer of the at least two layers has a different selective reflection band of the light while illuminated at the predetermined wavelength. In accordance with additional aspects of embodiments of the invention, the capsule material layer may be an embossed layer, for example, embossed with a logo.

In accordance with additional aspects of embodiments of the invention, each layer independently may be embossed layer. In accordance with aspects of embodiments of the invention, embossing at least one layer, for example, those layers which contain semi-reflective flakes or substantially fully reflective flakes, enhances the difficulty to reproduce the security device, thus preventing a counterfeiter from providing the same security features having the same properties in term of color shift effect and/or light trajectory.

Figure 6:
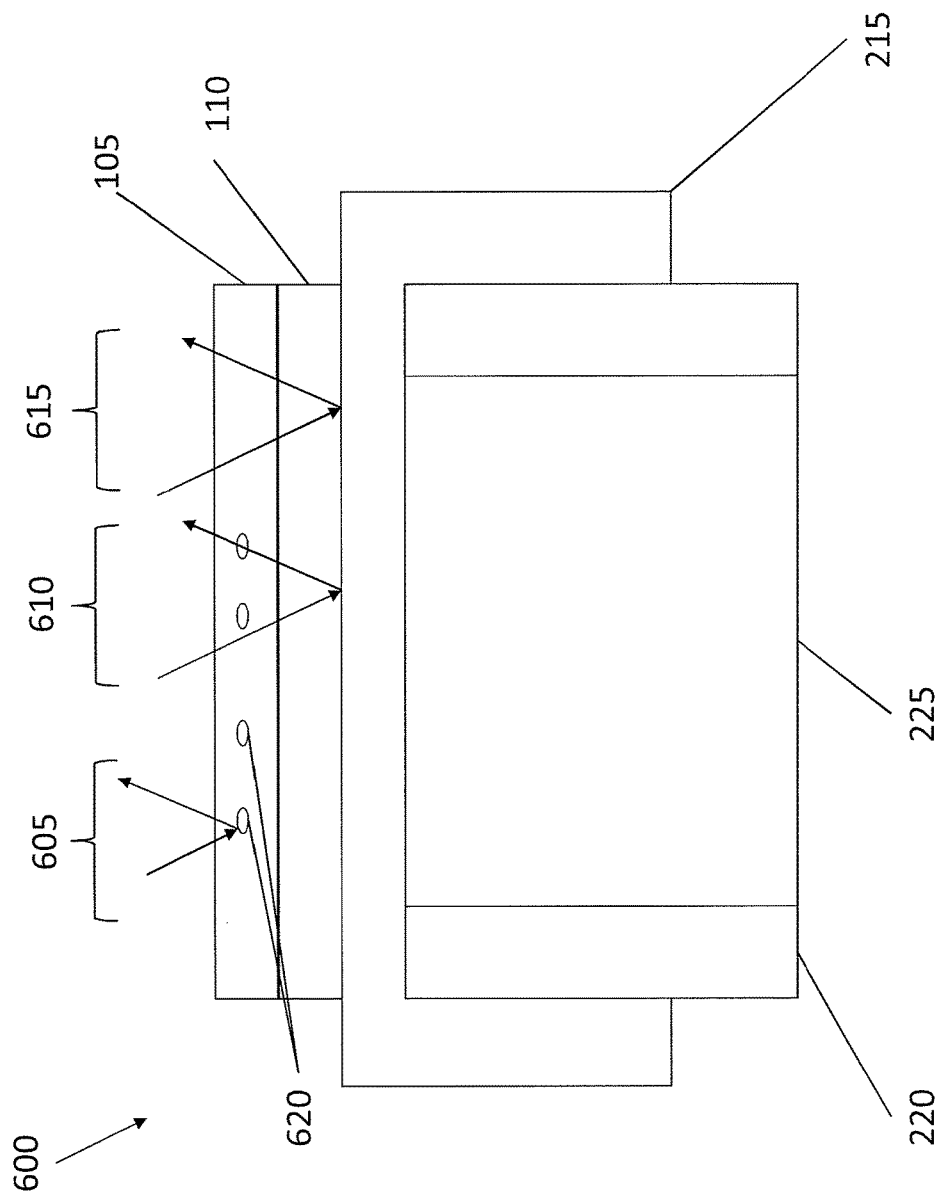
FIG. 6 illustrates exemplary light paths through one or more layers in accordance with embodiments of the invention.

FIG. 6 illustrates an exemplary capsule layer/bottle arrangement 600 depicting exemplary light paths 605, 610, 615 through one or more layers in accordance with embodiments of the invention. Exemplary capsule layer/bottle arrangement 600 includes a bottle 220 (e.g., a wine bottle), a cork 225 (e.g., a cork or synthetic plastic "cork") and a capsule material layer 215 arranged over the bottle 220 and cork 225. As shown with exemplary arrangement 600, a layer of ink 110 comprising flakes (not shown) having substantially full reflective properties is arranged (e.g., printed) on the capsule material layer 215. Additionally, with arrangement 600, a layer of ink 105 comprising flakes 620 having semi-reflective properties is arranged (e.g., printed) on the layer of ink 110.

As shown in FIG. 6, incident light may follow one of exemplary light paths 605, 610, 615 through one or more layers. For example, as shown in FIG. 6, with light path 605, incident light passes into the layer of ink 105 comprising flakes 620 having semi-reflective properties, is reflected off a flake 620 having semi-reflective properties, and passes out through the layer of ink 105.

With light path 615, incident light passing through the layer of ink 105 and into layer of ink 110 comprising flakes (not shown) having substantially full reflective properties, is reflected off a flake (not shown) having substantially full reflective properties, and passes out through the layer of ink 110 and layer of ink 105. In accordance with aspects of embodiments of the invention, a further additive layer luminescent layer (such as layer 230 as described above) may be placed before the layer 110 on the top of the capsule metal layer 215.

In accordance with additional aspects of embodiments of the invention, upon receiving the light, at least one layer comprising the flakes exhibiting full reflection is structured and arranged to provide a reflecting light to the at least one second layer to back light the at least one second layer. For example, with light path 610, incident light passes through the layer of ink 105 and into layer of ink 110 comprising flakes (not shown) having substantially full reflective properties is reflected off a flake (not shown) having substantially full reflective properties. In contrast to light path 615, however, light path 610 impact a flakes 620 having semi-reflective properties and provides a synergistic back-lighting effect to the layer of ink 105 comprising flakes 620 having semi-reflective properties. As mentioned previously, layers 110 and 105 (and luminescent layer, which is not shown in this exemplary arrangement) can be each independently embossed, or can all embossed collectively.

Partially Reflective Layer

In embodiments, the one or more layers may include a partially reflective layer. For example, the partially reflective layer may include a first composition having flakes exhibiting partial reflection of light received at a predetermined wavelength. In embodiments, the partially reflective layer may comprise one or more layers of at least one cholesteric liquid crystal polymer (CLCP). In embodiments, the one or more layers of CLCP comprise one or more layers of flakes of CLCP.

For example, with a CLCP layer, an unusual color shift, e.g. a color changing from green to red-violet, can be produced. Similarly, CLCP multilayers can be produced wherein the individual layers, having different reflection wavelengths, reflect light of a different sense of circular polarization. The resulting film, as well as the pigments produced there from, displays a first color to the unaided eye, and different second and third colors when viewed through left- or right-circular polarizing filters, respectively.

Additional non-limiting examples of materials for use in the present invention are flakes having at least one layer of CLCP. Such polymers reflect a circular polarized light component. Thus, within a determined wavelength range, light having a determined circular polarization state (left- or right-handed, depending on the polymer) is predominantly reflected. Cholesteric liquid crystal polymers have a molecular order in the form of helically arranged molecular stacks. This order is at the origin of a periodic spatial modulation of the material's refractive index, which in turn results in a selective transmission/reflection of determined wavelengths and polarizations of light. The particular situation of the helical molecular arrangement in CLCPs causes the reflected light to be circular polarized, left-handed or right-handed, depending on the sense of rotation of the molecular helical stack.

A marking, comprising a random distribution of CLCP flakes, provides the capsule (or the cork), for example, with a unique optical signature, detectable and distinguishable through its specific reflection of circular polarized light. The flakes can appear in random positions and orientations on the printed document or item. The marking, which can be almost transparent, but distinguishable from the background through its polarization effect, can be used in all types of authentication, identification, tracking and tracing applications, for all types of documents or goods. While inks comprising CLCP flakes, for example, are discussed herein as carriers for track-and-trace purposes, embodiments of the present invention also contemplate additional types of carriers for track-and-trace information, such as, for example, visible and infrared carriers. Embodiments of the invention contemplate visible and/or infrared track-and-trace carriers in addition to, or in place of the CLCP carriers.

Such CLCP flakes are obtainable from a corresponding CLCP multilayer film by breaking the film into the corresponding flakes by techniques known by those skilled in the art. The chiral liquid crystal polymer layer can be formed from a chiral liquid crystal precursor composition comprising (i) one or more (e.g. two, three, four, five or more and in particular, at least two) different nematic compounds A and (ii) one or more (e.g., two, three, four, five or more) different chiral dopant compounds B which are capable of giving rise to a cholesteric state of the chiral liquid crystal precursor composition upon heating. Further, both the one or more nematic compounds A and the one or more chiral dopant compounds B may comprise at least one compound which comprises at least one polymerizable group. For example, all of the one or more nematic compounds A and all of the one or more chiral dopant compounds B may comprise at least one polymerizable group. The at least one polymerizable group may, for example, comprise a group which is able to take part in a free radical polymerization and in particular, a (preferably activated) unsaturated carbon-carbon bond such as, e.g., a group of formula $H_2C=CH—C(O)—$.

The chiral liquid crystal precursor composition preferably comprises a mixture of: (i) one or more nematic (precursor) compounds A; and (ii) one or more cholesteric (i.e., chiral dopant) compounds B (including cholesterol), which are capable of giving rise to a cholesteric state of the composition. The pitch of the obtainable cholesteric state depends on the relative ratio of the nematic and the cholesteric compounds. Typically, the (total) concentration of the one or more nematic compounds A in the chiral liquid crystal precursor composition for use in the present invention, for example, will be about five to about twenty times the (total) concentration of the one or more cholesteric compounds B.

Nematic (precursor) compounds A which are suitable for use in the chiral liquid crystal precursor composition are known in the art; when used alone (i.e., without cholesteric compounds) they arrange themselves in a state characterized by its birefringence. Non-limiting examples of nematic compounds A that are suitable for use in the present invention are described in, e.g., WO 93/22397, WO 95/22586, EP-B-0 847 432, U.S. Pat. No. 6,589,445, US 2007/0224341 A1. The entire disclosures of these documents are incorporated by reference herein.

A preferred class of nematic compounds for use in the present invention comprises one or more (e.g., 1, 2 or 3) polymerizable groups, identical or different from each other, per molecule. Examples of polymerizable groups include groups that are capable of taking part in a free radical polymerization, and in particular, groups comprising a carbon-carbon double or triple bond such as, e.g., an acrylate moiety, a vinyl moiety or an acetylenic moiety. Particularly preferred as polymerizable groups are acrylate moieties.

The nematic compounds for use in the present invention further may comprise one or more (e.g., 1, 2, 3, 4, 5 or 6) optionally substituted aromatic groups, preferably phenyl groups. Examples of the optional substituents of the aromatic groups include those which are set forth herein as examples of substituent groups on the phenyl rings of the chiral dopant compounds of formula (I) such as, e.g., alkyl and alkoxy groups.

Examples of groups which may optionally be present to link the polymerizable groups and the aryl (e.g., phenyl) groups in the nematic compounds A include those which are exemplified herein for the chiral dopant compounds B of formula (I) (including those of formula (IA) and formula (IB) set forth below). For example, the nematic compounds A may comprise one or more groups of formulae (i) to (iii) which are indicated below as examples for $A_1$ and $A_2$ in formula (I) (and formulae (IA) and (IB)), typically bonded to optionally substituted phenyl groups. Specific non-limiting examples of nematic compounds which are suitable for use in the present invention are given below in the Example.

The one or more cholesteric (i.e., chiral dopant) compounds B for use in the present invention preferably comprise at least one polymerizable group. Suitable examples of the one or more chiral dopant compounds B include those of formula (I):

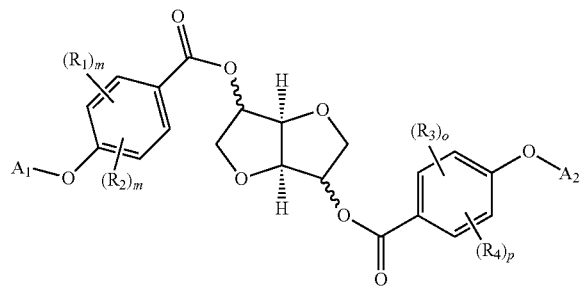
(I)

wherein:
$R_1$, $R_2$, $R_3$, $R_4$, $R_5$, $R_6$, $R_7$ and $R_8$ each independently denote $C_1$-$C_6$ alkyl and $C_1$-$C_6$ alkoxy;
$A_1$ and $A_2$ each independently denote a group of formula (i) to (iii):

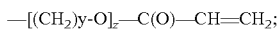  (i)

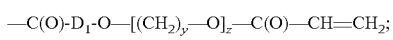  (ii)

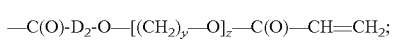  (iii)

$D_1$ denotes a group of formula

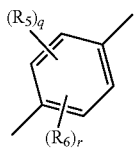

$D_2$ denotes a group of formula

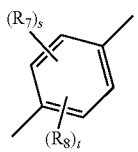

m, n, o, p, q, r, s, and t each independently denote 0, 1, or 2;
y denotes 0, 1, 2, 3, 4, 5, or 6;
z equals 0 if y equals 0 and z equals 1 if y equals 1 to 6.

In one embodiment, the one or more chiral dopant compounds B may comprise one or more isomannide derivatives of formula (IA):

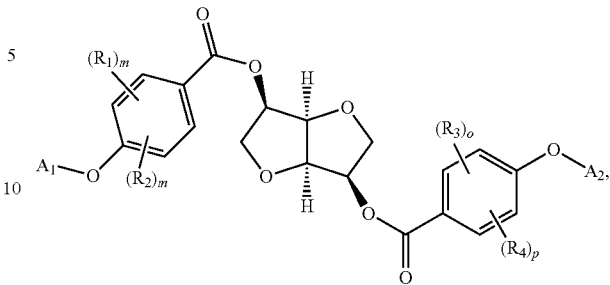
(IA)

wherein:
$R_1$, $R_2$, $R_3$, $R_4$, $R_5$, $R_6$, $R_7$ and $R_8$ each independently denote $C_1$-$C_6$ alkyl and $C_1$-$C_6$ alkoxy;
$A_1$ and $A_2$ each independently denote a group of formula (i) to (iii):

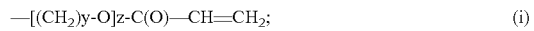  (i)

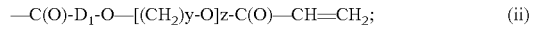  (ii)

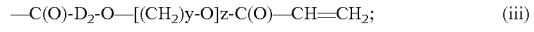  (iii)

$D_1$ denotes a group of formula

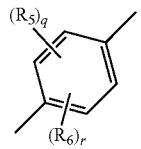

$D_2$ denotes a group of formula

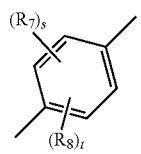

m, n, o, p, q, r, s, and t each independently denote 0, 1, or 2;
y denotes 0, 1, 2, 3, 4, 5, or 6;
z equals 0 if y equals 0 and z equals 1 if y equals 1 to 6.

In one exemplary embodiment of the compounds of formula (IA) (and of compounds of formula (I)), $R_1$, $R_2$, $R_3$, $R_4$, $R_5$, $R_6$, $R_7$ and $R_8$ each independently denote $C_1$-$C_6$ alkyl. In an alternative embodiment, $R_1$, $R_2$, $R_3$, $R_4$, $R_5$, $R_6$, $R_7$ and $R_8$ in formula (IA) (and in formula (I)) each independently denote $C_1$-$C_6$ alkoxy.

In another exemplary embodiment of the compounds of formula (I) and of formula (IA), $A_1$ and $A_2$ each independently denote a group of formula —[(CH$_2$)$_y$—O]$_z$—C(O)—CH=CH$_2$; $R_1$, $R_2$, $R_3$ and $R_4$ each independently denote $C_1$-$C_6$ alkyl; and m, n, o, and p each independently denote 0, 1, or 2. In yet another embodiment, $A_1$ and $A_2$ in formula (I) and formula (IA) each independently denote a group of formula —[(CH$_2$)$_y$—O]$_z$—C(O)—CH=CH$_2$; $R_1$, $R_2$, $R_3$ and $R_4$ each independently denote $C_1$-$C_6$ alkoxy; and m, n, o, and p each independently denote 0, 1, or 2.

In another embodiment of the compounds of formula (IA) (and of formula (I)), $A_1$ and $A_2$ each independently denote a group of formula —C(O)-$D_1$-O—[($CH_2$)$_y$—O]$_z$—C(O)—CH=$CH_2$ and/or of formula —C(O)-$D_2$-O—[($CH_2$)$_y$—O]$_z$—C(O)—CH=$CH_2$; and $R_1$, $R_2$, $R_3$, $R_4$, $R_5$, $R_6$, $R_7$ and $R_8$ each independently denote $C_1$-$C_6$ alkyl. In an alternative embodiment, $A_1$ and $A_2$ in formula (IA) (and in formula (I)) each independently denote a group of formula —C(O)-$D_1$-O—[($CH_2$)$_y$—O]$_z$—C(O)—CH=$CH_2$ and/or a group of formula —C(O)-$D_2$-O—[($CH_2$)$_y$—O]$_z$—C(O)—CH=$CH_2$; and $R_1$, $R_2$, $R_3$, $R_4$, $R_5$, $R_6$, $R_7$ and $R_8$ each independently denote $C_1$-$C_6$ alkoxy.

In another embodiment, the one or more chiral dopant compounds B may comprise one or more isosorbide derivatives represented by formula (IB):

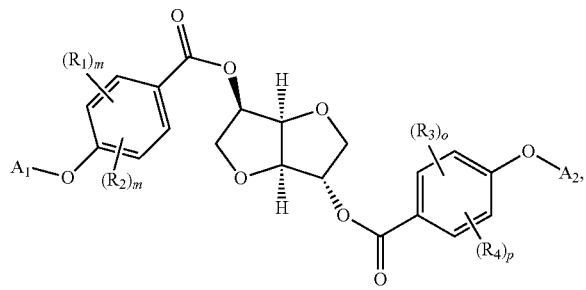

(IB)

wherein:
$R_1$, $R_2$, $R_3$, $R_4$, $R_5$, $R_6$, $R_7$ and $R_8$ each independently denote $C_1$-$C_6$ alkyl and $C_1$-$C_6$ alkoxy;
$A_1$ and $A_2$ each independently denote a group of formula (i) to (iii):

—[($CH_2$)y-O]z-C(O)—CH=$CH_2$;  (i)

—C(O)-$D_1$-O—[($CH_2$)y-O]z-C(O)—CH=$CH_2$;  (ii)

—C(O)-$D_2$-O—[($CH_2$)y-O]z-C(O)—CH=$CH_2$;  (iii)

$D_1$ denotes a group of formula

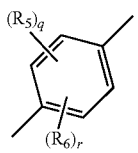

$D_2$ denotes a group of formula

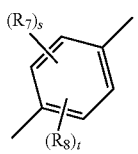

m, n, o, p, q, r, s, and t each independently denote 0, 1, or 2;
y denotes 0, 1, 2, 3, 4, 5, or 6;
z equals 0 if y equals 0 and z equals 1 if y equals 1 to 6.

In one embodiment of the compounds of formula (IB), $R_1$, $R_2$, $R_3$, $R_4$, $R_5$, $R_6$, $R_7$ and $R_8$ each independently denote $C_1$-$C_6$ alkyl. In an alternative embodiment, $R_1$, $R_2$, $R_3$, $R_4$, $R_5$, $R_6$, $R_7$ and $R_8$ in formula (IB) each independently denote $C_1$-$C_6$ alkoxy.

In another embodiment of the compounds of formula (IB), $A_1$ and $A_2$ each independently denote a group of formula —[($CH_2$)$_y$—O]$_z$—C(O)—CH=$CH_2$; $R_1$, $R_2$, $R_3$ and $R_4$ each independently denote $C_1$-$C_6$ alkyl; and m, n, o, and p each independently denote 0, 1, or 2. In yet another embodiment, $A_1$ and $A_2$ in formula (IB) each independently denote a group of formula —[($CH_2$)$_y$—O]$_z$—C(O)—CH=$CH_2$; $R_1$, $R_2$, $R_3$ and $R_4$ each independently denote $C_1$-$C_6$ alkoxy; and m, n, o, and p each independently denote 0, 1, or 2.

In another embodiment of the compounds of formula (IB), $A_1$ and $A_2$ each independently denote a group of formula —C(O)-$D_1$-O—[($CH_2$)$_y$—O]$_z$—C(O)—CH=$CH_2$ and/or of formula —C(O)-$D_2$-O—[($CH_2$)$_y$—O]$_z$—C(O)—CH=$CH_2$; and $R_1$, $R_2$, $R_3$, $R_4$, $R_5$, $R_6$, $R_7$ and $R_8$ each independently denote $C_1$-$C_6$ alkyl. In an alternative embodiment, $A_1$ and $A_2$ in formula (IB) each independently denote a group of formula —C(O)-$D_1$-O—[($CH_2$)$_y$—O]$_z$—C(O)—CH=$CH_2$ and/or a group of formula —C(O)-$D_2$-O—[($CH_2$)$_y$—O]$_z$—C(O)—CH=$CH_2$; and $R_1$, $R_2$, $R_3$, $R_4$, $R_5$, $R_6$, $R_7$ and $R_8$ each independently denote $C_1$-$C_6$ alkoxy.

In a preferred embodiment, the alkyl and alkoxy groups of $R_1$, $R_2$, $R_3$, $R_4$, $R_5$, $R_6$, $R_7$ and $R_8$ in formulae (I), (IA) and (IB) may comprise 3, 4, 6 or 7 carbon atoms and in particular, 4 or 6 carbon atoms.

Examples of alkyl groups comprising 3 or 4 carbon atoms include isopropyl and butyl. Examples of alkyl groups comprising 6 or 7 carbon atoms include hexyl, 2-methylpentyl, 3-methylpentyl, 2,2-dimethylpentyl, and 2,3-dimethylpentyl.

Examples of alkoxy groups comprising 3 or 4 carbon atoms include isopropoxy, but-1-oxy, but-2-oxy, and tert-butoxy. Examples of alkoxy groups comprising 6 or 7 carbon atoms include hex-1-oxy, hex-2-oxy, hex-3-oxy, 2-methylpent-1-oxy, 2-methylpent-2-oxy, 2-methylpent-3-oxy, 2-methylpent-4-oxy, 4-methylpent-1-oxy, 3-methylpent-1-oxy, 3-methylpent-2-oxy, 3-methylpent-3-oxy, 2,2-dimethylpent-1-oxy, 2,2-dimethylpent-3-oxy, 2,2-dimethylpent-4-oxy, 4,4-dimethylpent-1-oxy, 2,3-dimethylpent-1-oxy, 2,3-dimethylpent-2-oxy, 2,3-dimethylpent-3-oxy, 2,3-dimethylpent-4-oxy, and 3,4-dimethylpent-1-oxy.

The one or more chiral dopant compounds B will usually be present in a total concentration of from about 0.1% to about 30% by weight, e.g., from about 0.1% to about 25%, or from about 0.1% to about 20% by weight, based on the total weight of the composition. For example, in the case of inkjet printing the best results will often be obtained with concentrations of from 3% to 10% by weight, e.g., from 5% to 8% by weight, based on the total weight of the polymer composition. The one or more nematic compounds A will often be present in a concentration of from about 30% to about 50% by weight, based on the total weight of the polymer composition.

A chiral liquid crystal precursor composition use to obtain a chiral liquid crystal polymer layer will usually comprise a solvent to adjust its viscosity to a value which is suitable for the employed application method. Suitable solvents are known to those of skill in the art. Non-limiting examples thereof include low-viscosity, slightly polar and aprotic organic solvents, such as, e.g., methyl ethyl ketone (MEK), acetone, cyclohexanone, ethyl acetate, ethyl 3-ethoxypropionate, toluene, and mixtures of two or more thereof.

If a chiral liquid crystal precursor composition (comprising one more polymerizable monomers) is to be cured/polymerized by UV radiation the composition will also comprise at least one photoinitiator that shows a non-negligible solubility in the composition. Non-limiting examples of the many suitable photoinitiators include α-hydroxyketones such as 1-hydroxy-cyclohexyl-phenyl-ketone and a mixture (e.g., about 1:1) of 1-hydroxy-cyclohexyl-phenyl-ketone and one or more of benzophenone, 2-hydroxy-2-methyl-1-phenyl-1-propanone, and 2-hydroxy-1-[4-(2-hydroxyethoxy)phenyl]-2-methyl-1-propanone; phenylglyoxylates such as methylbenzoylformate and a mixture of oxy-phenyl-acetic acid 2-[2-oxo-2-phenyl-acetoxy-ethoxy]-ethyl ester and oxy-phenyl-acetic 2-[2-hydroxy-ethoxy]-ethyl ester; benzyldimethyl ketals such as alpha, alpha-dimethoxy-alpha-phenylacetophenone; α-aminoketones such as 2-benzyl-2-(dimethylamino)-1-[4-(4-morpholinyl)phenyl]-1-butanone and 2-methyl-1-[4-(methylthio)phenyl]-2-(4-morpholinyl)-1-propanone; phosphine oxide and phosphine oxide derivatives such as diphenyl (2,4,6-trimethylbenzoyl)-phosphine oxide; phenyl bis(2,4,6-trimethylbenzoyl) supplied by Ciba; and also thioxanthone derivatives such as Speedcure ITX (CAS 142770-42-1), Speedcure DETX (CAS 82799-44-8), Speedcure CPTX (CAS 5495-84-1-2 or CAS 83846-86-0) supplied by Lambson.

If a chiral liquid crystal precursor composition is to be cured by a method which is different from irradiation with UV light such as, e.g., by high-energy particles (e.g., electron beams), X-rays, gamma-rays, etc. the use of a photoinitiator can, of course, be dispensed with.

The at least two chiral liquid crystal polymer (CLCP) layers can comprise components A) and B), wherein A) is 20-99.5 wt % of at least one three-dimensionally crosslinkable compound of the formula (1)

$$Y^1\text{-}A^1\text{-}M^1\text{-}A^2\text{-}Y^2 \quad (1)$$

wherein $Y^1$, $Y^2$ are equal or different, and represent polymerizable groups;

$A^1$, $A^2$ are equal or different residues of the general formula $C_nH_{2n}$, wherein n is an integer between 0 and 20, and wherein at least one methylene group may be replaced by an oxygen atom;

$M^1$ has the formula $-R^1-X^1-R^2-X^2-R^3-X^3-R^4-$;

wherein $R^1$ to $R^4$ are equal or different bivalent residues chosen from the group consisting of $-O-$, $-COO-$, $-COHN-$, $-CO-$, $-S-$, $-C\equiv C-$, $CH-CH-$, $-N=N-$, $-N=N(O)-$, and a C—C bond; and wherein $R^2-X^2-R^3$ or $R^2-X^2$ or $R^2-X^2-R^3-X^3$ may as well be a C—C bond;

$X^1$ to $X^3$ are equal or different residues chosen from the group consisting of 1,4-phenylene; 1,4-cyclohexylene; heteroarylenes having 6 to 10 atoms in the aryl core and 1 to 3 heteroatoms from the group consisting of 0, N and S, and carrying substituents $B^1$, $B^2$ and/or $B^3$; cycloalkylenes having 3 to 10 carbon atoms and carrying substituents $B^1$, $B^2$ and/or $B^3$;

wherein $B^1$ to $B^3$ are equal or different substituents chosen from the group consisting of hydrogen, $C_1$-$C_{20}$-alkoxy, $C_1$-$C_{20}$-alkylthio, $C_1$-$C_{20}$-alkyl carbonyl, alkoxycarbonyl, $C_1$-$C_{20}$-alkylthiocarbonyl, $-OH$, $-F$, $-Cl$, $-Br$, $-I$, $-CN$, $-NO_2$, Formyl, Acetyl, and alkyl-, alkoxy-, or alkylthio-residues with 1 to 20 carbon atoms having a chain interrupted by ether oxygen, thioether, sulfur or ester groups; and B) is 0.5 to 80 wt % of at least one chiral compound of the formula (2)

$$V^1\text{-}A^1\text{-}W^1\text{-}Z\text{-}W^2\text{-}A^2\text{-}V^2 \quad (2)$$

wherein $V^1$, $V^2$ are equal or different and represent a residue of the following: acrylate, methacrylate, epoxy, vinyl ether, vinyl, isocyanate, $C_1$-$C_{20}$-alkoxy, alkylthio, $C_1$-$C_{20}$-alkylcarbonyl, $C_1$-$C_{20}$-alkoxycarbonyl, $C_1$-$C_{20}$-alkylthiocarbonyl, $-OH$, $-F$, $-Cl$, $-Br$, $-I$, $-CN$, $-NO_2$, Formyl, Acetyl, as well as alkyl-, alkoxy-, or alkylthio-residues with 1 to 20 carbon atoms having a chain interrupted by ether oxygen, thioether sulfur or ester groups, or a cholesterol residue;

$A^1$, $A^2$ are as indicated above;

$W^1$, $W^2$ have the general formula $-R^1-X^1-R^2-X^2-R^3-$, wherein $R^1$ to $R^3$ are as indicated above, and wherein $R^2$ or $R^2-X^2$ or $X^1-R^2-X^2-R^3$ may also be a C—C bond;

$X^1$, $X^2$ are as indicated above;

Z is a divalent chiral residue chosen from the group consisting of dianhydrohexites, hexoses, pentoses, binaphthyl derivatives, biphenyl derivatives, derivatives of tartaric acid, and optically active glycols, and a C—C bond in the case where $V^1$ or $V^2$ is a cholesterol residue.

The component B) can be selected from at least one of AnABIs-(2-[4-(acryloyloxy)-benzoyl]-5-(4-methoxybenzoyl)-isosorbid), DiABIs (di-2,5-[4-(acryloloxy)-benzoyl]-isosorbid), and DiABIm (di-2,5[(4'-acryl oyloxy)-benzoyl]-isomannid).

A flake may be made, for example, by first preparing a CLCP multilayer film with properties as discussed above, and thereafter comminuting (e.g., chopping, crushing, etc.) the film to thereby form multilayer flakes, as disclosed, for example, in US 2010/0178508 A1 or US 2010/0200649 A1, which are incorporated by reference in their entireties herein. For example, the polymerized CLCP film is detached from a carrier and the cover foil through a peeling, scratching, brushing or other operation. The resulting, coarse CLCP flakes are worked up into pigment using known comminuting operations, such as milling with hammer-, impact-, ball-, or jet-mills, and classified by known separation methods such as triage and sieving, in order to obtain a pigment with specified particle size, having a d50-value in an application-specified range between 5 and 5000 micrometer. The average diameter can be between 3 to 30 times the total layer thickness of the flake In addition to a determined reflection color, the cholesteric liquid crystal polymer (CLCP) shows also a more or less pronounced viewing-angle dependent color variation ("color shift.") Films and pigments made of CLCP are for this reason suitable as security elements on value and identity documents, because the color-shifting effect cannot be reproduced by photocopying machines.

A number of different reflection colors can be realized with a same given CLCP precursor material through appropriately choosing the manufacturing conditions. Further to this, the handiness (left- or right-handed) of the reflection can be chosen as well through the appropriate choice of the chirality inducing additive at the time of manufacturing the material.

In embodiments, the CLCP layer exhibits high brilliance and viewing-angle dependent color change (color-flip effect), as well as particular reflection properties, such as, for example, a color change from a short-wavelength to a long-wavelength color in going from orthogonal to oblique view, or an extremely long travel in color space in response to a changing viewing angle.

With embodiments of the present invention, the optical properties of the CLCP layer can be tuned very precisely. The process and the materials allow for a more accurate production of a determined CLCP's spectral reflection profile, because the profile can be precisely composed by superposing an appropriate numbers of layers, each layer having its characteristic narrow band reflection profile at a pre-set wavelength. This allows coding a pigment with an invisible, narrow-band spectral feature, which, for example, does not show up as a visible appearance, but which can be evidenced with the help of a spectrometer or a particular optical filter device.

The fact that the reflected light of a CLCP is circularly polarized can be used as a further security element. The sense of this circular polarization is determined through the manufacturing process. The circular polarization handiness can be chosen individually for each layer of the multilayer CLCP, and this polarization handiness can be evidenced with the help of a corresponding polarization filter. It is thus possible to give any layer of the multilayer CLCP an individual narrow-band reflection color, and individual polarization handiness.

For example, with the CLCP pigment, an unusual color shift, e.g. a color changing from green to red-violet, can be produced. Similarly, CLCP multilayers can be produced wherein the individual layers, having different reflection wavelengths, reflect light of a different sense of circular polarization. The resulting film, as well as the pigments produced there from, displays a first color to the unaided eye, and different second and third colors when viewed through left- or right-circular polarizing filters, respectively. For example, in a particular embodiment of a security element, a first layer of the CLCP multilayer reflects a first color, e.g. green, of left-circular polarized light, and a second layer of the CLCP multilayer reflects a second color, e.g. red, of right-circular polarized light. There will be a first visible color displayed by the security element to the unaided eye, which is composed of both reflections, e.g. green and red; the resulting appearance is yellow. Viewed under a left-circular polarizing filter, however, the same security element will appear green, and viewed under a right-circular polarizing filter, it will correspondingly appear red.

The differing optical property is preferably a wavelength of maximal reflection and/or a circular polarization state. It may, however, also comprise optical absorption or luminescence properties, such as can be obtained through the admixture of dyes, pigments or luminescent compounds to one of the CLCP layers of the multilayer, or an adjacent luminescent layer, as discussed below. The CLCP flakes can further comprise an additional layer made with luminescent and/or magnetic material.

Embodiments of the present invention may utilize CLCP flakes having an exemplary three-layer configuration as follows: $L_1/L_2/L_3$, wherein $L_1$ and $L_3$ are each chiral liquid crystal polymer layers having respective reflectances of $\lambda_1 max$ and $\lambda_2 max$, (which could be the same or different), and wherein $L_2$ is a layer made with luminescent and/or magnetic materials with specific optical or magnetic properties. Such flakes provide a high level of coding properties. For example, different sizes of flakes may be used, with different luminescent properties, and/or with different circular polarization properties for layers $L_1$ and $L_3$. This high level of coding properties reinforces the protection of the cork or the capsule in the context of the present invention and drastically limits the possibility of a counterfeiter to reproduce the capsule or the cork with such a high level of protection.

The number of realizable different optical responses can be substantially increased if different CLCP pigment types, having different optical responses, are combined with each other in a same ink. The production of a security element in such case depends on the availability of two or more different pigments, which are mixed together in the appropriate ratios for serving a determined security document application.

The security level of the CLCP material could be further increased, if the different optical responses could be combined into a same physical pigment, because it is much easier to make up an ink comprising a mixture of a few modular pigments having basic optical responses (i.e. to combine letters of an alphabet), than to manufacture a single pigment which combines optical basic responses into a more complex response (i.e. to find a determined word). Whereas the former can essentially be done in any printer's shop, if the basic pigments are available, the latter can only be performed at the pigment manufacturing facility, and enables therefore a control of the pigment supply chain.

With additional contemplated embodiments, the flakes, when incorporated in a coating material, such as a resin or ink, can be deposited on a substrate in a random distribution by a suitable technique, such as a printing technique, such as inkjet printing or spraying techniques. This makes possible the creation of a unique code which can be based on, e.g., the random distribution of the flakes and/or different sizes of flakes and/or a unique distribution of a color shift effect and/or based on the properties of the one or more detectable elements that may be present in the flakes, including any one of the layers of the flake, such as one or more of the chiral liquid crystal polymer layers.

The method can include marking a substrate (e.g., a capsule material), wherein the method comprises providing the substrate with a marking comprising a plurality of coding flakes; reading deterministic data and/or non-deterministic data, such as non-deterministic data representative of at least distribution of the plurality of coding flakes in the marking; and recording and storing in a computer database the deterministic and/or non-deterministic data, such as non-deterministic data representative of at least distribution of the plurality of coding flakes in the marking.

The method can also include identifying and/or authenticating a substrate, article of value or item, wherein the method comprises reading deterministic data and/or non-deterministic data of a marking associated with the substrate including a plurality of coding flakes; and comparing using a database through a computer the read data with stored data of the deterministic and/or non-deterministic data, such as non-deterministic data representative of at least distribution of the plurality of coding flakes in the marking.

The non-deterministic data can comprise the distribution of flakes or the plurality of flakes within the marking. Moreover, the non-deterministic property can be random sizes of flakes in one or more markings. A marking, comprising a random distribution of circular polarizing particles, (such as can be applied to an item (e.g., a capsule) via coating a composition comprising CLCP flakes), provides the item with a unique optical signature, detectable and distinguishable through detectable parameters.

As disclosed in US 2010/200649 A1, the entire disclosure of which is incorporated by reference herein in its entirety, the method of marking and identifying or authenticating an item can comprise the steps of a) providing an item with a random distribution of particles, (the particles being chosen from any embodiments of the flakes as disclosed herein); b) recording and storing, at a first point in time, data representative of the random distribution of flakes, using a reading device comprising illumination elements and optical detectors; c) identifying or authenticating the marked item at a later point in time using a reading device as in step b) and the stored data representative of the random distribution of particles. In embodiments, the reading devices of step b) and c), while they can be the same device, need not to be the same device, nor of the same type of device. In accordance with aspects of embodiments of the present invention, the method can use CLCP flakes that reflect a circular polarized light component, preferably in at least one spectral area chosen from the ultraviolet, the visible, and the infrared electromagnetic spectrum, i.e., between approximately 300 nm and 2500 nm wavelength.

The term "reading device" designates a device which is capable of identifying or authenticating a document or item marked with the flake and/or film as disclosed herein. In addition to this, the reading device may have other capabilities, such as that of reading barcodes, taking images, etc. The reading device may in particular be a modified barcode reader, camera mobile phone, an electronic tablet or pad, an optical scanner, etc. The reading can be performed with a reading device comprising at least illumination elements and optical detection elements, and can include magnetic properties detection elements depending upon parameters to be determined. The device can contain all the elements able to capture all the information and/or there can be multiple devices able to capture only or more properties from one to another, and all collected information will be after a post treatment linked together to generated the code.

In accordance with aspects of the invention, one or more layers printed on the capsule layer may include a layer of partially reflective flakes, e.g., CLCP flakes (e.g., a CLCP pigment layer). The optical security markings have the advantage to show, in addition to the visible color shifting effect with changing viewing angle, an invisible circular polarization effect, which can be evidenced with the help of a corresponding instrument.

The pigments of the present invention are preferably used in printing inks for the silk-screen, flexo, offset, and gravure printing processes; however, offset, copperplate intaglio and tampographic printing processes are considered as well.

In embodiments, the multilayer structure may include one or more partially reflective layers, as described above.

Substantially Fully Reflective Layer

In embodiments, the one or more layers may include a substantially fully reflective layer. For example, the substantially fully reflective layer may include a composition having flakes exhibiting substantially full reflection of light received at a predetermined wavelength. In embodiments, the substantially fully reflective layer may comprise one or more layers of optically variable pigments (OVP), which exhibit a viewing angle dependent shift of color.

OVPs have proven effective as an efficient, printable anti-copy device on bank notes and security documents since 1987. Today, a large part of the worldwide printed currency relies on optically variable copy protection devices, and among these latter, optically variable ink (OVI™) has acquired a preeminent place.

The viewing-angle dependent shift of color cannot be reproduced by color copying equipment. Various different types of OVP materials are commercially available today, all depending on interference thin film structures. The hue, the color travel and the chromaticity of the structures however depend upon on the material constituting the layers, the sequence and the number of layers and, the layer thickness, as well as on the production process.

Very brilliant colors are obtained with a first type of OVP, made by physical vapor deposition (PVD) according to e.g. U.S. Pat. Nos. 4,705,300; 4,705,356; 4,721,217; 4,779,898; 4,930,866; and 5,084,351, the entire disclosures of which are incorporated by reference herein. This OVP is constructed as a thin-film vapor-deposited Fabry-Perot resonator stack. Simple-sandwich metal-dielectric-metal, as well as double-sandwich metal-dielectric-metal-dielectric-metal layer sequences are described. The middle metal layer can be realized as opaque totally reflecting layer to yield a maximum in reflectivity of the incident light. The top metal layer(s) must be partially transparent, such that light can be coupled in and out of the Fabry-Perot resonator.

Incident light falling upon an optically variable pigment flake of said metal-dielectric-metal type is partially reflected at the top metal layer. Another portion of the light travels through the dielectric and is reflected at the bottom metal layer. Both reflected parts of the incident light finally recombine and interfere with each other. Constructive or destructive interference results, depending on the thickness of the dielectric layer and on the wavelength of the incident light. In the case of white incident light, some of the light components, having determined wavelengths, are reflected, whereas other components, having other wavelengths, are not reflected. This gives rise to a spectral selection, and hence to the appearance of color.

The path difference between the top-reflected and the bottom-reflected part of the light depends on the angle of incidence, and so does the resulting interference color.

Another, second type of OVP, made according to EP 708,154; DE 195,25,503; U.S. Pat. Nos. 5,624,468, 5,401, 306; 4,978,394; and 4,344,987, the entire disclosures of which are incorporated by reference herein, is based on coated aluminum flakes. Mechanically flattened aluminum particles are coated by chemical vapor deposition (CVD) or by wet chemical methods with a dielectric layer and a subsequent metal or second dielectric layer. Interference colors result by the same effect as described above.

In embodiments of the present invention optically variable pigments (OVP), which may be used in at least one layer in the marking of the invention, may comprise apart from the viewing angle dependent color shift, additional features resulting in a response upon exposure to external energy.

The OVP pigments comprise an interference structure of at least two thin film layers of different materials, and exhibit a viewing angle dependent shift of color. In embodiments, at least one of said layers comprises at least one luminescent material. The OVP may have a structure comprising at least one light-transmitting dielectric layer with a first and a second surface essentially parallel to each other and at least one semi-transparent, partially reflecting layer arranged on each of said first and second surfaces of the dielectric layer with the luminescent material being comprised in at least one of the dielectric layers. The OVP may also have a structure comprising an opaque totally reflecting layer having first and second surfaces essentially parallel to each other and at least one sequence arranged on at least one of said first and second surfaces of the opaque totally reflecting layer. The sequence comprises at least one dielectric layer and at least one semi-transparent partially reflecting layer with the dielectric layer of the sequence being adjacent to the totally reflecting layer and the luminescent material being comprised in at least one of the dielectric layers.

The partially reflecting and partially transmitting top layer has a thickness in the range of 5 to 25 nm. Preferably the semi-transparent partially reflecting layer is chosen from metal, metal-oxides or metal-sulfides such as aluminum, chromium, $MoS_2$, $Fe_2O_3$. The dielectric layer is of a low refractive index material having an index of refraction not exceeding 1.50, under the precondition that the material does not comprise luminescent material. Preferably the material is chosen from $MgF_2$, $SiO_2$, and $AlF_3$. Low refractive index dielectrics result in a high angle-dependent color shift. The thickness of the dielectric depends on the desired OVP color; it is of the order of 200 to 600 nm. For example, gold-to-green OVP, e.g., has an $MgF_2$ layer of 440 nm in thickness, and green-to-blue OVP includes an $MgF_2$ layer of 385 nm in thickness. The opaque totally reflecting layer is selected from metals or metal alloys such as aluminum, silver, copper, cobalt-nickel alloy, aluminum alloys. Most preferred is aluminum with a reflectivity of nearly 99% over the whole spectral domain of interest. The totally reflecting layer has a thickness in the range of 50 to 150 nm. Pigments of the latter type can have a symmetric $Cr/MgF_2/Al/MgF_2/Cr$ structure, in order to yield equal reflecting properties for both sides. The central aluminum layer acts as a total reflector. In the context of the present invention it is sufficient to consider the half of the OVP structure, i.e. the basic $Cr/MgF_2/Al$ stack. These pigments consist of flakes, which are of the order of 20 to 30 μm large, and about 1 μm of thickness.

The dielectric layer may not contain luminescent ions, and in this case are considered as a part of OVP of first order. The OVP of first order may have additional luminescent ions, wherein the luminescent ions are incorporated into a dielectric coating applied to the aluminum flakes, to yield OVP (also named OVP of a second type). Said dielectric coating can again be applied either by chemical vapor deposition, e.g., using a fluidized-bed reactor, or alternatively, by wet chemical methods, as known by those ordinarily skilled in the art. The color-shifting properties of these types of OVP are related to the realizable path difference, within the dielectric, between orthogonal incidence and grazing incidence. The incident beam is diffracted according to Snell's law, $n_1*\sin(\alpha)=n_2*\sin(\beta)$, where $n_1$ and $n_2$ are the respective refraction indices of the materials 1 and 2, and α and β are the respective beam angles to the normal. Assuming $n_1=1$ (air), the grazing angle incidence ($\alpha=90°$) condition is described as $\sin(\beta)=1/n_2$. The maximum length of the light path L within the dielectric, in terms of the dielectric thickness d, is then given by $L=d/\sqrt{1-1/n_2^2}$.

The dielectric layer of the OVP flake can comprise at least one luminescent ion. Especially interesting for the purpose of the present invention are the trivalent ions of certain transition elements such as chromium ($Cr^{3+}$), iron ($Fe^{3+}$), etc. Particularly preferred are rare-earth ions. Preferably the rare earths ions are selected from the group consisting of yttrium ($Y^{3+}$), praseodymium ($Pr^{3+}$), neodymium ($Nd^{3+}$), samarium ($Sm^{3+}$), europium ($Eu^{3+}$), terbium ($Tb^{3+}$), dysprosium ($Dy^{3+}$), holmium ($Ho^{3+}$), erbium ($Er^{3+}$), thulium ($Tm^{3+}$) and ytterbium ($Yb^{3+}$).

Such doping is not easily practicable with $MgF_2$ as the dielectric, because of the relatively small ionic radius of the $Mg^{2+}$ ion (72 pm), compared to the radii of the trivalent rare-earth ions (86-102 pm), and of the simultaneous need for charge compensation. Although the co-evaporation of $MgF_2$ with trivalent rare earth fluorides yields chemically doped materials, the narrow $MgF_2$ host lattice cannot accommodate for the strain induced by the voluminous doping ions, which tend in consequence to form clusters. Clustered excited rare-earth ions undergo rapid non-radiative deactivation, and no luminescence is observed.

The dielectric layer containing the luminescent material is selected from the group consisting of difluorides of the second main group or zinc or cadmium, or of mixtures thereof. In a preferred embodiment, $CaF_2$ is used as dielectric material to be doped with trivalent rare-earths, in particular lanthanoides, due to the comparable ionic radii of $Ca^{2+}$ (100 pm) and of the $Ln^{3+}$ ions. The positive excess charge of the $Ln^{3+}$ dopant must be compensated, however. Charge compensation can be brought about either anionically, by replacing a fluoride ion ($F^-$ 133 pm) by an oxide ion ($O^{2-}$, 140 pm), or cationically, by replacing a calcium ion ($Ca^{2+}$, 100 pm) by a sodium ion ($Na^+$, 102 pm). Anionic compensation is easily achieved by annealing the material in oxygen, but may not be practicable in the presence of a heat-sensitive carrier web. Cationic compensation requires a carefully controlled, simultaneous co-doping with equal amount of $Ln^{3+}$ and $Na^+$ ions during the sputtering process.

Dielectric materials, also allowing for an easy incorporation of the luminescent material in particular the trivalent rare-earth ions (however without charge compensation), are selected from the group consisting of trifluorides of rare earths, trifluorides of bismuth, or mixtures thereof, complex fluorides of trivalent rare earth ions or bismuth and monovalent alkaline ions or divalent alkaline-earth or transition ions, in particular zinc and mixtures thereof. Particularly preferred are trifluorides of yttrium and in particular the non-luminescent ions, i.e. $YF_3$, $LaF_3$, $CeF_3$, $GdF_3$, $LuF_3$, and $BiF_3$ or, alternatively, among their complex fluorides, e.g. $ALnF_4$, $AeLn_2F_8$, $ALn_3F_{10}$, etc., wherein A is a monovalent alkaline ion, preferably selected among $Li^+$, $Na^+$, $K^+$; Ae is a divalent alkaline-earth or transition ion, preferably selected among $Mg^{2+}$, $Ca^{2+}$, $Sr^{2+}$, $Ba^{2+}$, $Zn^{2+}$, and Ln is a trivalent rare-earth ion, preferably selected among $Y^{3+}$, $La^{3+}$, $Ce^{3+}$, $Gd^{3+}$, or $Bi^{3+}$. In the context of the present invention, the pure trifluorides or mixtures thereof are preferable over said complex fluorides, because the evaporation characteristics of the former can be better controlled.

For the incorporation of luminescent material, in particular of the trivalent transition element ions, dielectric materials are selected from the group consisting of trifluorides of elements of the third main group or bismuth or of trivalent transition element ions or mixtures thereof, complex fluorides of elements of the third main group or bismuth and an alkaline ion, an alkaline-earth ion or zinc or mixtures thereof. Particularly adapted are $EF_3$ materials, wherein E is $Al^{3+}$, $Ga^{3+}$, $In^{3+}$, $Bi^{3+}$, or a trivalent transition element ion or $Na_3AlF_6$.

Fluoride materials are the preferred dielectric hosts for said luminescent ions. Fluorides have a low-energy optical phonon spectrum, i.e., their IR absorption bands are situated at low energy. Under such circumstances, the vibrational deactivation of the embedded excited luminescent ions is strongly inhibited, resulting in a high luminescence yield and in long-lived excited states. Fluorides are, furthermore, a rather uncommon host matrix in commercially available luminescents. This adds favorably to the security potential of the present invention. The luminescent ions incorporated in the OVP can in this way be distinguished, e.g., by their specific luminescence decay times, from simple mixtures of commercial luminescents and non-security optically variable ink.

In any case, OVP having luminescence centers incorporated within the Fabry-Perot resonance cavity can be distinguished from simple mixtures of non-luminescent OVP (and added luminescent material) by their angle-dependent excitation spectrum. That is, the OVP's resonance cavity internally amplifies the incident light intensity for wavelengths corresponding to the minima of the cavity's reflection characteristics, i.e., for $n*d=k*.\lambda/2$, the laser resonator condition. At these wavelengths, the cavity preferably takes up energy from the environment, and the light intensity inside the cavity reaches a multiple of the outside intensity. Thus, a luminescent material situated within the cavity will be more strongly excited at the cavity's resonance condition than out of this condition. Because the cavity's resonance wavelength is angle-dependent, the luminescence intensities obtained for different incidence angles of the same exciting radiation will be different, which makes it possible to determine that the luminescent is located within the OVP's cavity rather than outside of it.

The deposition of the luminescent dielectric layer can be performed by the same method as used for the deposition of the $MgF_2$ layer. For example, the $MgF_2$ can be deposited from a hot semi-melt by electron beam sputtering. Rare-earth fluorides are more or less comparable in melting point and evaporation characteristics with $MgF_2$, and can therefore be deposited by the very same technique. The doping elements can be added in beforehand to the matrix fluoride; e.g., 2% of $EuF_3$ can be pre-melted with 98% of $LaF_3$ to form a homogeneous mixture, and this mixture may be used as a depositing material. To compensate for an eventual decrease in angle-dependent color-shift caused by the presence of the $LnF_3$ layer, the $MgF_2$ part of the dielectric can be replaced, according to embodiments of the invention, by an $AlF_3$ layer. $AlF_3$ has a lower index of refraction (n=1.23) than $MgF_2$ (n=1.38), and thus, can easily compensate for the introduction of an equivalent layer of $LaF_3$ (n=1.55).

In the context of the embodiments of the present invention, the at least one layer which is a substantially fully reflective layer comprises OVP flakes which can be OVP flakes of first or second order or mixtures thereof. It is also noted that the OVP used in the context of the present invention and which are part of the substantially fully reflective layer, is not limited to those cited above. For example, one skilled in the art can use other known OVP flakes in the context of the present invention.

One of the advantages of using OVP flakes is the fact that the OVP layer will provide a substantially fully reflective layer which will backlight the partially reflective layer located above. The corresponding perception of the flakes that comprise the partially reflective layer (e.g., with a dedicated device) will be enhanced, and could additionally serve as a basis for a fingerprint recognition. Moreover, as this effect is hard to reproduce, this bonus effect adds to the high security level of the capsule or the cork protected according to the present invention.

Luminescent Layer

In embodiments, the one or more layers may include a luminescent layer. For example, the luminescent layer may include a luminescent pigment. The term "luminescence" as used herein refers to the process in which light is emitted from a material at a different wavelength than that which is absorbed. It is an umbrella term covering both fluorescence and phosphorescence. The term "fluorescence" as used herein refers to a luminescence phenomenon in which electron de-excitation occurs almost spontaneously, and in which emission from a luminescent substance ceases when the exciting source is removed. In fluorescent materials, the excited state has the same spin as the ground state. A compound capable of fluorescence is termed a "fluor". The term "phosphorescence" as used herein refers to a quasi-stable electron excitation state involving a change of spin state (intersystem crossing) which decays only slowly. In phosphorescence, light emitted by an atom or molecule persists after the exciting source is removed. It is similar to fluorescence, but the species is excited to a metastable state from which a transition to the initial state is forbidden. Emission occurs when thermal energy raises the electron to a state from which it can de-excite. Therefore, phosphorescence is temperature-dependent. The term phosphorescence thus refers to a delayed luminescence or sustained glowing after exposure to energized particles such as electrons or ultraviolet photons, that is, a luminescence that persists after removal of the exciting source. It is sometimes called afterglow. A compound capable of phosphorescence is termed a "phosphor".

Luminescent compounds in pigment form have been widely used in inks and other preparations (see U.S. Pat. No. 6,565,770, WO08033059, WO08092522, the entire disclosures of which are incorporated by reference herein). Examples of luminescent pigments can be found in certain classes of inorganic compounds, such as the sulphides, oxysulphides, phosphates, vanadates, garnets, spinels, etc. of nonluminescent cations, doped with at least one luminescent cation chosen from the transition-metal or the rare-earth ions.

Suitable luminescent compounds that could be incorporated in the luminescent layer according to the present invention can be found in US2010/0307376 which relates to rare-earth metal complexes, the entire disclosure of which is incorporated by reference herein. The rare-earth metal complexes are chosen from the luminescent lanthanide complexes of trivalent rare-earth ions with three dinegatively charged, tridentate 5- or 6-membered heteroaryl ligands. The luminescent ink may comprise a stable, water-soluble tris-complex of a trivalent rare-earth cation with an atomic number between 58 and 70, such as, for example: Pr, Nd, Sm, Eu, Gd, Tb, Dy, Ho, Er, Tm, Yb and the mixtures thereof, with a tridentate, dinegatively charged heteroaryl ligand that absorb in the ultraviolet and/or the blue region of the electromagnetic spectrum. The luminescent emission in these lanthanide complexes is due to inner f-shell transitions such as: 5D0→7F1 and 5D0→7F2 for Eu(3+).

The corresponding luminescent lanthanide complex is of the formula:

wherein M is chosen from the alkali cations Li+, Na+, K+, Rb+ and Cs+ and the mixtures thereof;

wherein Ln is chosen from the trivalent rare-earth cations of Ce, Pr, Nd, Sm, Eu, Gd, Tb, Dy, Ho, Er, Tm, and Yb;

and wherein A is a dinegatively charged, tridentate 5- or 6-membered heteroaryl ligand, such as the dipicolinate anion, in which the complex has an exact 1:3 (Ln:A) stoichiometry and the dinegatively charged, tridentate 5- or 6-membered heteroaryl ligand A is selected from the group consisting of pyridine, imidazole, triazole, pyrazole, pyrazine bearing at least one carboxylic acid group. The 5 to 6 membered heteroaryl of the present invention bearing at least one carboxylic group can be further substituted by a group hydroxyl, amino, a C1-C6-alkoxy, such as a methoxy, ethoxy, isopropoxy, etc. group or a C1-C6-alkyl, such as a methyl, ethyl, isopropyl, etc. group.

As described in Patent Application Publication No. US2010/0307376, the entire disclosure of which has been incorporated by reference herein, a particular process for imprinting secure document with luminescent compounds, in particular luminescent rare-earth metal complexes, is inkjet printing, and more particularly thermal inkjet printing. Thermal inkjet printers use print cartridges having a series of tiny electrically heated chambers, constructed by photolithography.

To produce an image, the printer sends a pulse of electric current through heating elements disposed in the back of each chamber, causing a steam explosion in the chamber, so as to form a bubble, which propels a droplet of ink through an orifice of the chamber onto the paper in front of it (hence the tradename Bubblejet® for certain inkjet printers). The ink's surface tension, as well as the condensation and thus contraction of the vapor bubble, pulls a further charge of ink into the chamber through a narrow channel attached to a specific aqueous inkjet composition comprising at least one specific class of rare earth metal complexes in a specific ratio.

Other suitable luminescent compounds which could be incorporated in the luminescent layer according to the present invention are described in Patent Application Publication No. US2011/0293899, the entire disclosure of which is incorporated by reference herein. As described in Patent Application Publication No. US2011/0293899, a class of compounds that is suitable for use in, e.g., printing inks for marking purposes are perylene dyes, including perylene dyes with increased solubility. The parent compound perylene displays blue fluorescence and there are many derivatives of perylene which are known and may theoretically be employed as colorants in compositions for marking such as printing inks and the like. Quaterrylene, Terrylene derivatives and/or a colored material, such as riboflavine or flavoinoids, which have also the advantages to be non-toxic, are also suitable luminescent compounds which can be used in the context of embodiments of the present invention.

The intended purpose of the printing ink composition is one of several factors which determines suitable and desirable concentration ranges for the polymer-bonded perylene dye(s) as well as the types and concentration ranges of suitable or desirable optional components of the composition. There are many different types of printing processes. Non-limiting examples thereof include inkjet printing (thermal, piezoelectric, continuous, etc.), flexography, intaglio printing (e.g., gravure printing), screen printing, letterpress printing, offset printing, pad printing, relief printing, planographic printing and rotogravure printing. In a preferred embodiment, a printing ink composition in accordance with the present invention is suitable (at least) for inkjet printing. (Industrial inkjet printers, commonly used for numbering, coding and marking applications on conditioning lines and printing presses, are particularly suitable. Preferred ink-jet printers include single nozzle continuous ink-jet printers (also called raster or multi-level deflected printers) and drop-on-demand ink jet printers, in particular valve-jet printers.)

In embodiments, the multilayer structure may include one or more luminescent layers, as described above and each layer may additionally contain one or more luminescent compounds with different chemical and/or physical properties. Above cited examples of luminescent compounds are non-limiting examples in the context of the present invention. In embodiments, the luminescent layer containing the luminescent compounds used in the context of the present invention could be a partially opaque layer or an opaque layer.

Exemplary Embodiments

Figure 7:
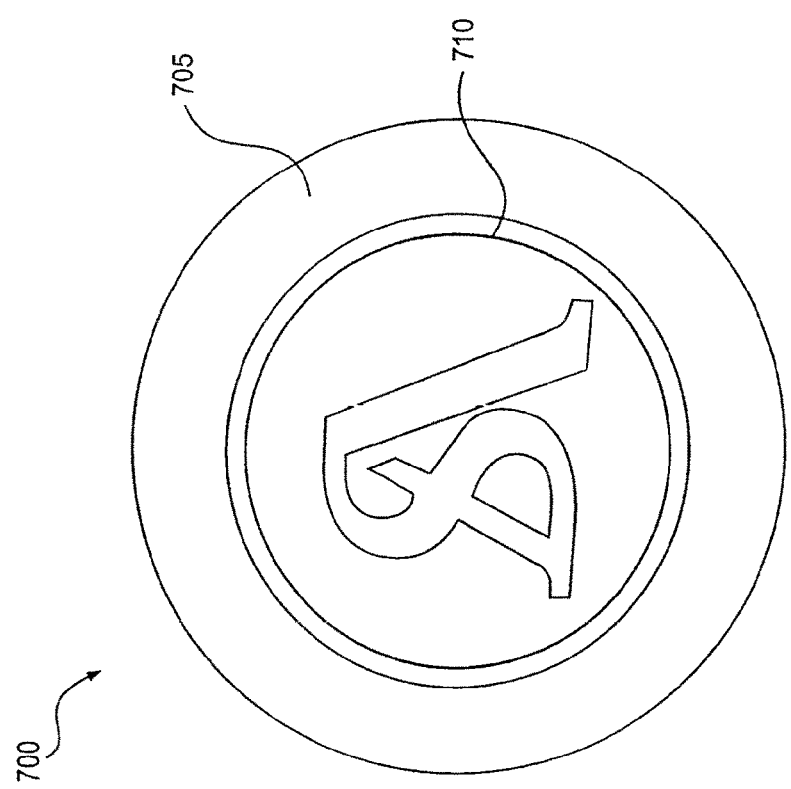
FIGS. 7 and 8 are photographs of exemplary capsule layer/ink layer combinations in accordance with embodiments of the invention.
Figure 8:
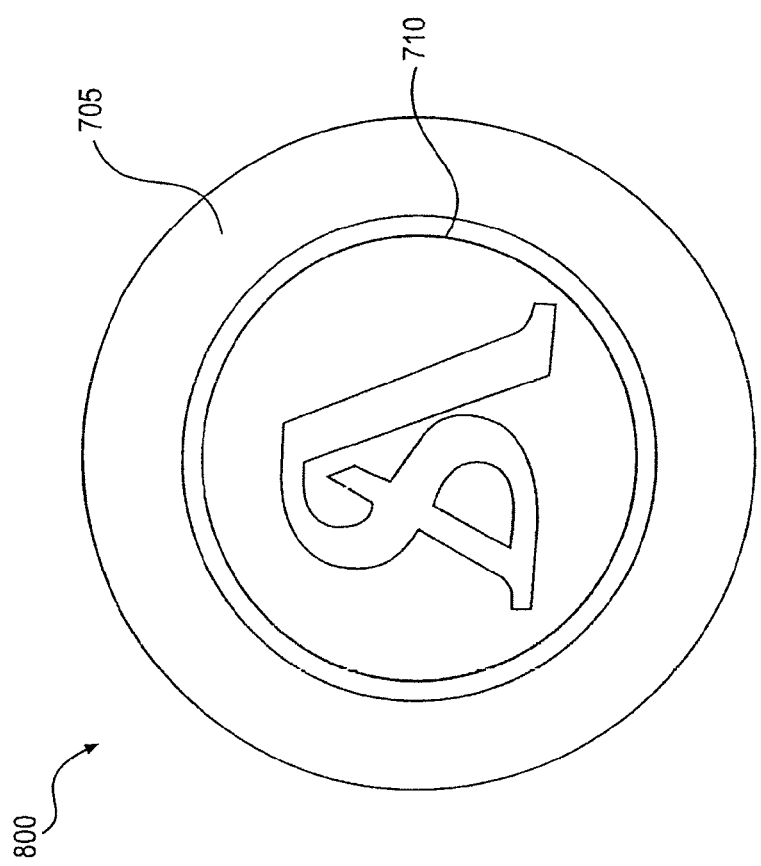

FIGS. 7-8 are photographs of exemplary capsule layer/ink layer combinations in accordance with embodiments of the invention.

FIG. 7 is a photograph of an exemplary capsule layer/ink layer combination 700 in accordance with embodiments of the invention. Capsule layer/ink layer combination 700 includes a capsule material substrate layer 705 comprising a polylaminate printed with solvent gravure black and includes an embossed image (e.g., logo) with ring 710. Capsule layer/ink layer combination 700 additionally includes a plurality of ink layers printed as set forth in TABLE 1.

TABLE 1

Printing Sequence:

| LAYERS | DESCRIPTION |
| --- | --- |
| 1$^{st}$ down | ink comprising flakes having semi-reflective properties (e.g., WB Gravure ink with CLCP Flakes Neutral DL MR) |
| 2$^{nd}$ down | ink comprising flakes having substantially full reflective properties (e.g., Offset Form Roller with OVP flakes Pink/Green rolled) over embossed area only |

Exemplary Formulations:
WB ink with CLCP Flakes Neutral DL

| Acrylic Polymer | 41.61 |
| --- | --- |
| Acrylic Polymer | 22.19 |
| Surfactant | 2.20 |
| Defoamer | 1.00 |
| Water | 5.00 |
| Optical Pigment | 12.50 |
| Optical Pigment | 12.50 |
| Upconverter | 3.00 |

Offset Form Roller Ink with OVP Flakes Pink/Green

| Wet Offset Transparent White Base | 37.00 |
| --- | --- |
| Alkyd Resin | 41.00 |
| Optical Pigment | 14.60 |
| Optical Pigment | 5.40 |
| Offset Ink Drier | 2.0 |

The successful offset form roller printing of the ink comprising flakes having substantially full reflective properties (e.g., with OVP flakes pigments), can be considered an unexpected result as these pigments have previously not successfully printed in an offset multi-roller system.

In accordance with aspects of embodiments of the present invention, a variation is observable (and detectable) in the color shift colors of the ink comprising flakes having substantially full reflective properties (e.g., with OVP flakes_pink/green) depending if viewing this layer overprinted on the portion having ink comprising flakes having semi-reflective properties (e.g., with CLCP Flakes_Neutral DL) or where overprinted on the black capsule material substrate layer 705 only.

In accordance with additional aspects of embodiments of the present invention, distinctiveness as a fully layered security device could be enhanced by adding one or more additional layers of the following security inks:
  a) WB Gravure Invisible Fluorescent inks,
  b) infrared absorbing (IRA) black, infrared transparent (IRT) black or a combination of IRA/IRT black pairs alone or as an under print for inks with CLCP Flakes and/or with OVP flakes, and/or
  c) Invisible and/or visible, serialized and/or non-serialized datacode on capsule.

FIG. 8 is a photograph of an exemplary capsule layer/ink layer combination 800 in accordance with embodiments of the invention. Capsule layer/ink layer combination 800 includes a capsule material substrate layer 705 comprising a polylaminate printed with solvent gravure black and includes an embossed image (e.g., logo) with ring 710. Capsule layer/ink layer combination 800 additionally includes a plurality of ink layers printed as set forth in TABLE 2.

TABLE 2

Printing Sequence:

| LAYERS | DESCRIPTION |
| --- | --- |
| 1st down | ink comprising flakes having semi-reflective properties (e.g., WB Gravure ink with CLCP Flakes Green/Blue DL MR) |
| 2nd down | ink comprising flakes having substantially full reflective properties (e.g., Offset Form Roller ink with OVP flakes Pink/Green rolled over embossed area only) |

Exemplary Formulation:
  WB ink with CLCP Flakes Green/Blue DL

| Acrylic Polymer | 41.61 |
| --- | --- |
| Acrylic Polymer | 22.19 |
| Surfactant | 2.20 |
| Defoamer | 1.00 |
| Water | 5.00 |
| Optical Pigment | 16.00 |
| Optical Pigment | 9.00 |
| Upconverter | 3.00 |

The successful offset form roller printing of the ink comprising flakes having substantially full reflective properties (e.g., with OVP flakes), can be considered an unexpected result as these pigments have previously not successfully printed in an offset multi-roller system.

In accordance with aspects of embodiments of the present invention, a variation is observable (and detectable) in the color shift colors of the ink comprising flakes having substantially full reflective properties (e.g., with OVP flakes pink/green) depending if viewing this layer overprinted on the portion having ink comprising flakes having semi-reflective properties (e.g., CLCP flakes Green/Blue DL MR) or where overprinted on the black capsule material substrate layer 705 only.

In accordance with additional aspects of embodiments of the present invention, distinctiveness as a fully layered security device could be enhanced by adding one or more additional layers of the following security inks:
  a) WB Gravure Invisible Fluorescent inks,
  b) IRA black, IRT black or a combination of IRA/IRT black pairs alone or as an under print inks with CLCP Flakes and/or with OVP flakes, and/or
  c) Invisible and/or visible, serialized and/or non-serialized datacode on capsule.

While embodiments of the present invention have been described in the context of bottles (e.g., wine bottles), it should be understood that the present invention contemplates other types of containers, e.g., pharmaceutical containers and beverage containers of any variety. The exemplary embodiments shown in this present invention are non-limiting, and do not limit the scope of the invention in any manner, and are for illustrative purposes.

System Environment

As will be appreciated by one skilled in the art, embodiments of the present invention may be embodied as a system, a method or a computer program product. Accordingly, embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following:
  an electrical connection having one or more wires,
  a portable computer diskette,
  a hard disk,
  a random access memory (RAM),
  a read-only memory (ROM),
  an erasable programmable read-only memory (EPROM or Flash memory),
  an optical fiber,
  a portable compact disc read-only memory (CDROM),
  an optical storage device,
  a transmission media such as those supporting the Internet or an intranet,
  a magnetic storage device
  a usb key, and/or
  a certificate.

In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network. This may include, for example, a local area network (LAN) or a wide area network (WAN), or the connection may be made to an external computer (for example, through the Internet using an Internet Service Provider). Additionally, in embodiments, the present invention may be embodied in a field programmable gate array (FPGA).

Figure 9:
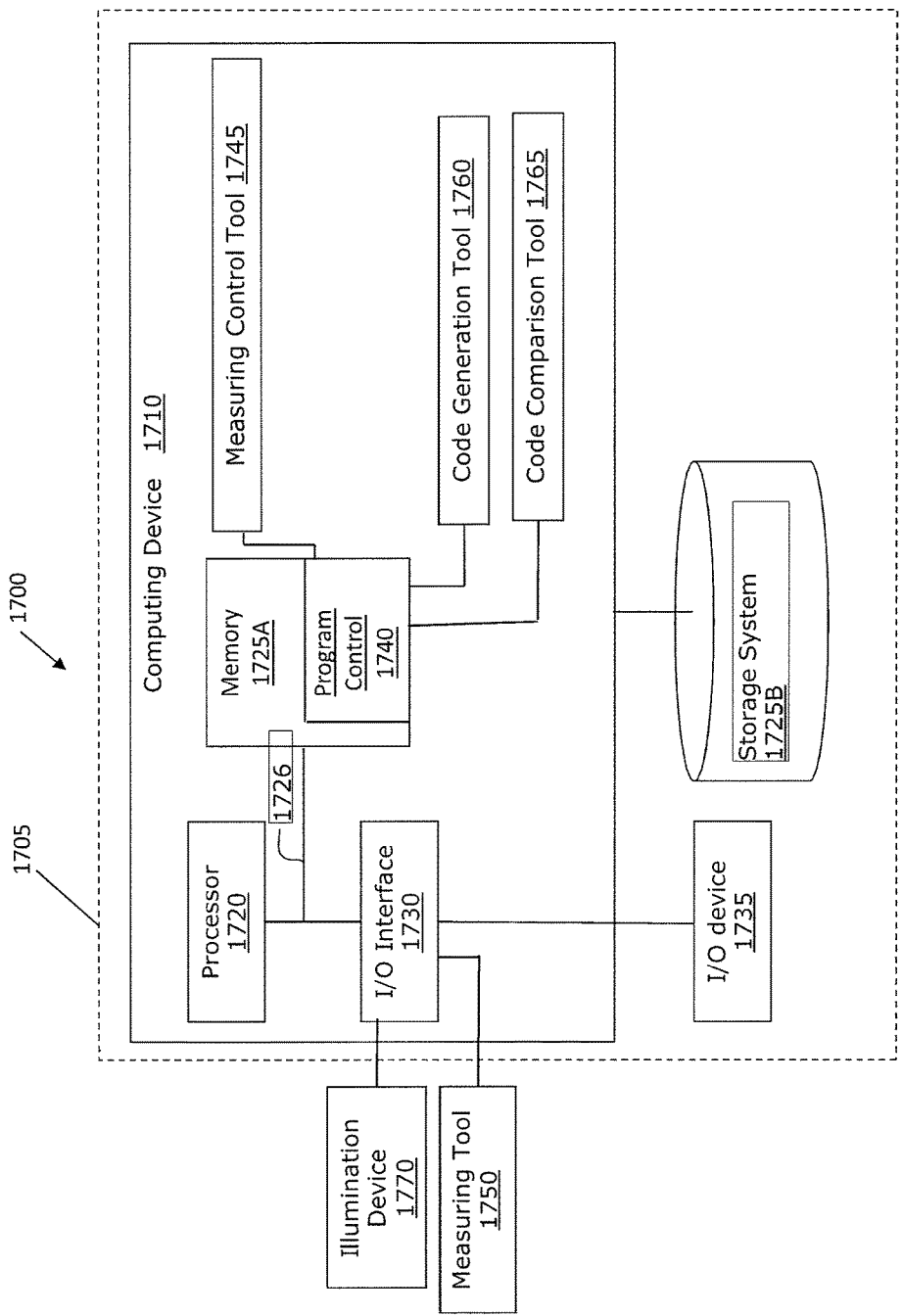
FIG. 9 shows an illustrative environment for managing the processes in accordance with embodiments of the invention.

FIG. 9 shows an illustrative environment 1700 for managing the processes in accordance with the invention. To this extent, the environment 1700 includes a server or other computing system 1705 that can perform the processes described herein. In particular, the server 1705 includes a computing device 1710. The computing device 1710 can be resident on a network infrastructure or computing device of a third party service provider (any of which is generally represented in FIG. 9).

In embodiments, the computing device 1710 includes one or more measuring control tools 1745 in communication with one or more measuring tools 1750, a code generation tool 1760, and a code comparison tool 1765, which are operable to measure reflected light and/or emitted light, generate an identification code based on measured properties or measured codes, and compare measured properties or measured codes with stored properties or stored codes, e.g., the processes described herein. The one or more measuring control tools 1745, the code generation tool 1760, and the code comparison tool 1765 can be implemented as one or more program code in the program control 1740 stored in memory 1725A as separate or combined modules.

The computing device 1710 also includes a processor 1720, memory 1725A, an I/O interface 1730, and a bus 1726. The memory 1725A can include local memory employed during actual execution of program code, bulk storage, and cache memories which provide temporary storage of at least some program code in order to reduce the number of times code must be retrieved from bulk storage during execution. In addition, the computing device includes random access memory (RAM), a read-only memory (ROM), and an operating system (O/S).

The computing device 1710 is in communication with the external I/O device/resource 1735 and the storage system 1725B. For example, the I/O device 1735 can comprise any device that enables an individual to interact with the computing device 1710 or any device that enables the computing device 1710 to communicate with one or more other computing devices using any type of communications link. The external I/O device/resource 1735 may be for example, a handheld device, PDA, handset, keyboard, smartphone, etc. Additionally, in accordance with aspects of the invention, the environment 1700 includes an illumination device 1770 for providing illumination, and one or more measuring tools 1750.

In general, the processor 1720 executes computer program code (e.g., program control 1740), which can be stored in the memory 1725A and/or storage system 1725B. Moreover, in accordance with aspects of the invention, the program control 1740 having program code controls the one or more measuring control tools 1745, the code generation tool 1760, the code comparison tool 1765, the one or more measuring tools 1750, and the illumination device 1770. While executing the computer program code, the processor 1720 can read and/or write data to/from memory 1725A, storage system 1725B, and/or I/O interface 1730. The program code executes the processes of the invention. The bus 1726 provides a communications link between each of the components in the computing device 1710.

The computing device 1710 can comprise any general purpose computing article of manufacture capable of executing computer program code installed thereon (e.g., a personal computer, server, etc.). However, it is understood that the computing device 1710 is only representative of various possible equivalent-computing devices that may perform the processes described herein. To this extent, in embodiments, the functionality provided by the computing device 1710 can be implemented by a computing article of manufacture that includes any combination of general and/or specific purpose hardware and/or computer program code. In each embodiment, the program code and hardware can be created using standard programming and engineering techniques, respectively.

Similarly, the computing infrastructure 1705 is only illustrative of various types of computer infrastructures for implementing the invention. For example, in embodiments, the server 1705 comprises two or more computing devices (e.g., a server cluster) that communicate over any type of communications link, such as a network, a shared memory, or the like, to perform the process described herein. Further, while performing the processes described herein, one or more computing devices on the server 1705 can communicate with one or more other computing devices external to the server 1705 using any type of communications link. The communications link can comprise any combination of wired and/or wireless links; any combination of one or more types of networks (e.g., the Internet, a wide area network, a local area network, a virtual private network, etc.); and/or utilize any combination of transmission techniques and protocols.

Flow Diagrams

Figure 10:
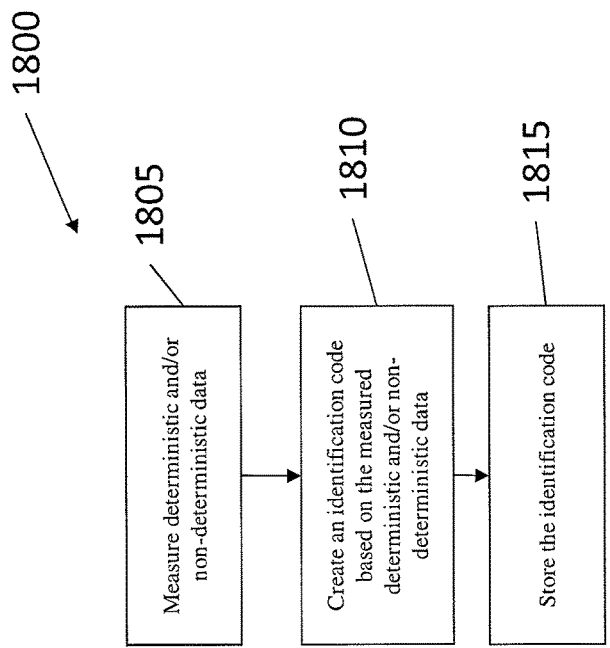
FIGS. 10 and 11 show exemplary flows for performing aspects of embodiments of the invention.
Figure 11:
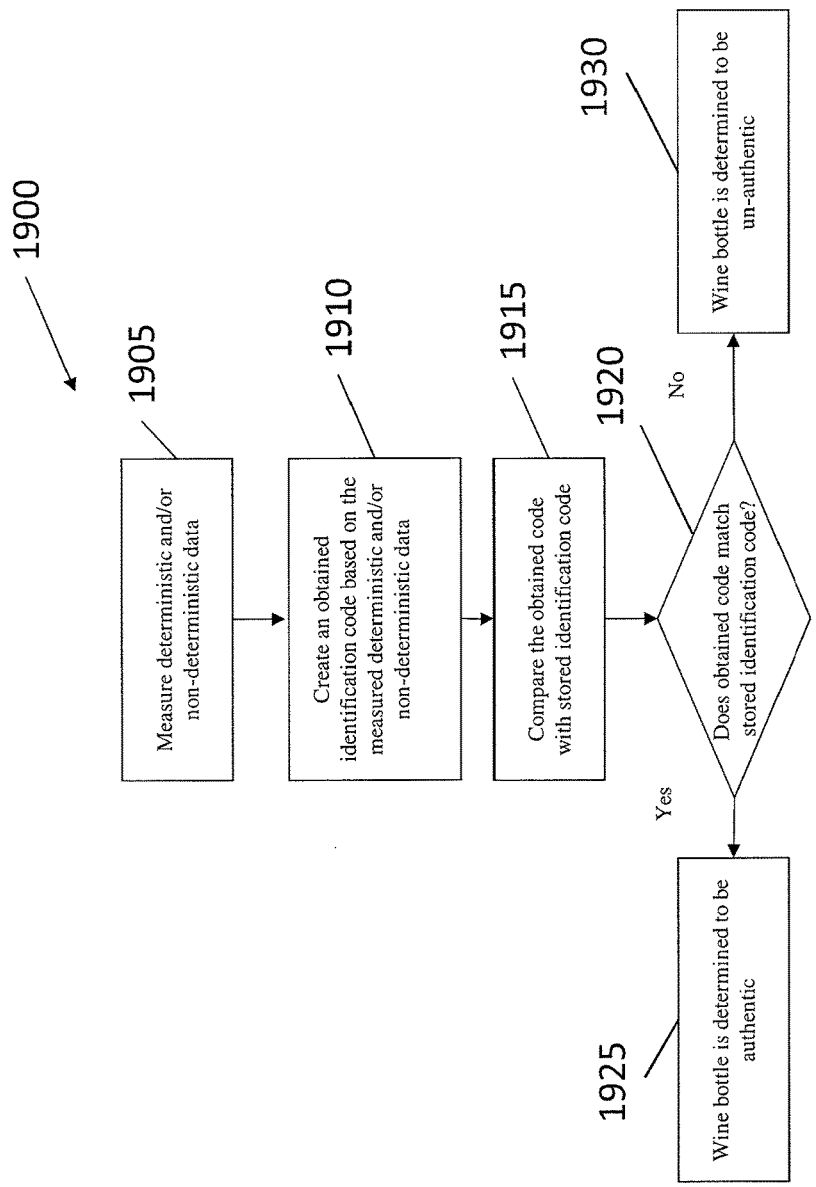

FIGS. 10 and 11 show exemplary flows for performing aspects of the present invention. The steps of FIGS. 10 and 11 may be implemented in the environment of FIG. 9, for example. The flow diagrams may equally represent high-level block diagrams of embodiments of the invention. The flowcharts and/or block diagrams in FIGS. 10 and 11 illustrate the architecture, functionality, and operation of possible implementations of systems, methods and computer program products according to various embodiments of the present invention. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of each flowchart, and combinations of the flowchart illustrations can be implemented by special purpose hardware-based systems that perform the specified functions or acts, or combinations of special purpose hardware and computer instructions and/or software, as described above. Moreover, the steps of the flow diagrams may be implemented and executed from either a server, in a client server relationship, or they may run on a user workstation with operative information conveyed to the user workstation. In an embodiment, the software elements include firmware, resident software, microcode, etc.

Furthermore, the invention can take the form of a computer program product accessible from a computer-usable or computer-readable medium providing program code for use by or in connection with a computer or any instruction execution system. The software and/or computer program product can be implemented in the environment of FIG. 9. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable storage medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disc-read/write (CD-R/W) and DVD.

FIG. 10 illustrates an exemplary flow 1800 for creating and storing an identification code for a wine bottle. At step 1805, the measuring tool measures deterministic and/or non-deterministic data, such as non-deterministic data representative of at least distribution of the plurality of coding flakes in the marking. At step 1810, the code generation tool creates an identification code based on the deterministic and/or non-deterministic data. At step 1815, the code generation tool stores the identification code in a storage system, e.g., a database.

FIG. 11 illustrates an exemplary flow 1900 for authentication and/or identification of a wine bottle. As shown in FIG. 11, at step 1905, the measuring tool measures deterministic and/or non-deterministic data. At step 1910, the code creation tool creates an obtained identification code based on the measured deterministic and/or non-deterministic data. At step 1915, the code comparison tool compares the obtained code with stored identification codes. At step 1920, the code comparison tool determines whether the obtained code matches a stored identification code. If, at step 1920, the code comparison tool determines that the obtained code matches a stored identification code, at step 1925, the wine bottle is determined to be authentic. If, at step 1920, the code comparison tool determines that the obtained code match does not match a stored identification code, at step 1930, the wine bottle is determined to be un-authentic.

While the invention has been described with reference to specific embodiments, those skilled in the art will understand that various changes may be made and equivalents may be substituted for elements thereof without departing from the true spirit and scope of the invention. In addition, modifications may be made without departing from the essential teachings of the invention.

What is claimed is:

1. A capsule placed on a beverage bottle, comprising:
    a capsule material layer having an interior surface structured and arranged for contact with the beverage bottle and an exterior surface; and
    at least two layers of security ink on the exterior surface of the capsule material layer,
    wherein each of the at least two layers has a different chemical composition, and
    wherein at least one layer of the at least two layers comprises a first composition having flakes exhibiting full reflection of light received at a predetermined wavelength.

2. The capsule according to claim 1, wherein at least one second layer of the at least two layers comprises a second composition having flakes exhibiting semi-reflection of light received at the predetermined wavelength.

3. The capsule according to claim 2, wherein the flakes exhibiting the semi-reflection constitute between about 3 to 25% based on a total weight of the second composition.

4. The capsule according to claim 1, further comprising a luminescent layer comprising a third composition containing at least one luminescent pigment.

5. The capsule according to claim 4, wherein the at least one luminescent pigment is comprised in said luminescent layer between 3 to 25% based on a total weight of the third composition.

6. The capsule according to claim 1, wherein the flakes exhibiting full reflection constitute between about 3 to 25% based on a total weight of the first composition.

7. A cork arrangement placed in a beverage bottle, comprising:
    a cork material layer; and
    at least two layers of security ink on the cork material layer,
    wherein each of the at least two layers has a different chemical composition, and
    wherein at least one layer of the at least two layers comprises a first composition having flakes exhibiting full reflection of light received at a predetermined wavelength.

8. The cork arrangement according to claim 7, wherein at least one second layer of the at least two layers comprises a second composition having flakes exhibiting semi-reflection of the light received at the predetermined wavelength.

9. The cork arrangement according to claim 7, further comprising a luminescent layer comprising a third composition containing at least one luminescent pigment.

10. The cork arrangement according to claim 7, further comprising a receiving layer.

11. A method of authenticating a capsule placed on a beverage bottle, the capsule comprising:
    a capsule material layer having an interior surface structured and arranged for contact with the beverage bottle and an exterior surface; and
    at least two layers of security ink on the exterior surface of the capsule material layer,
    wherein each of the at least two layers has a different chemical composition, and
    wherein at least one layer of the at least two layers comprises a first composition having flakes exhibiting full reflection of light received at a predetermined wavelength, the method comprising:
    illuminating the capsule with the light at the predetermined wavelength;
    detecting a reflected light, which is reflected by the at least one layer comprising the flakes exhibiting the full reflection and transmitted through the at least one second layer as a back light to the at least one second layer; and
    comparing the reflected light to a predetermined value to authenticate the capsule.

12. A multilayer structure, comprising:
    a capsule material layer having an interior surface structured and arranged for contact with the beverage bottle and an exterior surface; and at least two layers of security ink on the exterior surface of the capsule material layer, wherein each of the at least two layers has a different composition, and wherein at least one layer of the at least two layers comprises a first composition containing flakes exhibiting full reflection of light received at a predetermined wavelength.

13. The multilayer structure according to claim 12, wherein at least one second layer of the at least two layers comprises a second composition containing flakes exhibiting semi-reflection of light received at the predetermined wavelength.

14. The multilayer structure according to claim 12, further comprising a luminescent layer comprising a third composition containing at least one luminescent pigment.

15. The multilayer structure according to claim 14 wherein the luminescent layer is arranged in contact with the capsule material layer.

16. A capsule or cork to be used as a closure of a container comprising a multilayer structure according to claim 12.

17. A capsule or cork to be used as a closure of a beverage bottle comprising a multilayer structure according to claim 12.

18. A container comprising a closure, wherein the closure comprises the cork according to claim 17.

19. The container according to claim 18, further comprising a receiving layer arranged in contact with the container, such that at least a portion of the receiving layer is damaged upon removal of the cork from the container.

20. A container according to claim 19, wherein the container is a beverage bottle.

21. A capsule comprising a multilayer structure according to claim 12.

22. A container comprising a closure, wherein the closure comprises the capsule according to claim 21.

23. The container according to claim 22, wherein the capsule material layer is structured and arranged on the container such that at least a portion of the capsule material layer is damaged upon removal of the capsule material layer from the container.

24. A method of authenticating a cork placed on a container, the cork comprising:

a cork material layer; and at least two layers of security ink on the cork material layer, wherein each of the at least two layers has a different chemical composition, and wherein at least one layer of the at least two layers comprises a first composition having flakes exhibiting full reflection of light received at a predetermined wavelength, the method comprising:

illuminating the cork with the light at the predetermined wavelength;

detecting a reflected light, which is reflected by the at least one layer comprising the flakes having the full reflection and transmitted through the at least one second layer as a back light to the at least one second layer; and comparing the reflected light to a predetermined value to authenticate the cork.

* * * * *